United States Patent
Hughes et al.

(10) Patent No.: US 9,889,142 B2
(45) Date of Patent: *Feb. 13, 2018

(54) PROSTAMIDE-CONTAINING INTRAOCULAR IMPLANT

(71) Applicant: Allergan, Inc., Irvine, CA (US)

(72) Inventors: Patrick M. Hughes, Aliso Viejo, CA (US); Jie Shen, Irvine, CA (US); Michael R. Robinson, Irvine, CA (US); David F. Woodward, Lake Forest, CA (US); Robert M. Burk, Laguna Beach, CA (US); Hui Liu, Irvine, CA (US); Jinping Wan, Irvine, CA (US); Chandrasekar Durairaj, Lexington, MA (US); Gyorgy F. Ambrus, Santa Ana, CA (US); Ke Wu, Irvine, CA (US); Danny T. Dinh, Costa Mesa, CA (US)

(73) Assignee: Allergan, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/075,922

(22) Filed: Mar. 21, 2016

(65) Prior Publication Data
US 2016/0199387 A1    Jul. 14, 2016

Related U.S. Application Data

(63) Continuation of application No. 14/211,265, filed on Mar. 14, 2014, now Pat. No. 9,289,413.
(Continued)

(51) Int. Cl.
*A61K 31/55* (2006.01)
*A61K 31/559* (2006.01)
(Continued)

(52) U.S. Cl.
CPC .......... *A61K 31/559* (2013.01); *A61K 9/0051* (2013.01); *A61K 9/146* (2013.01);
(Continued)

(58) Field of Classification Search
None
See application file for complete search history.

(56) References Cited

U.S. PATENT DOCUMENTS

| 5,688,819 A | 11/1997 | Woodward et al. |
| 5,741,810 A | 4/1998 | Burk |

(Continued)

FOREIGN PATENT DOCUMENTS

| WO | 1995-018102 | 7/1995 |
| WO | 1996-036599 | 11/1996 |

(Continued)

OTHER PUBLICATIONS

Heinrich Stahl, Pharmaceutical Salts, Handbook of Pharmaceutical Salts, 2002, 329-345, International Union of Pure and Applied Chemistry, Verlag Helvetica Chemica Acta-Zürich.
(Continued)

*Primary Examiner* — Robert A Wax
*Assistant Examiner* — Melissa S Mercier
(74) *Attorney, Agent, or Firm* — Laura L. Wine

(57) ABSTRACT

Prostamide-containing biodegradable intraocular implants, prostamide compounds, prostamide-containing pharmaceutical compositions, and methods for making and using such implants and compositions for the immediate and sustained reduction of intraocular pressure and treatment of glaucoma in an eye of a patient are described.

3 Claims, 10 Drawing Sheets

Related U.S. Application Data

(60) Provisional application No. 61/798,291, filed on Mar. 15, 2013, provisional application No. 61/877,573, filed on Sep. 13, 2013, provisional application No. 61/898,210, filed on Oct. 31, 2013.

(51) Int. Cl.
   *A61K 31/381* (2006.01)
   *A61K 9/00* (2006.01)
   *A61L 27/18* (2006.01)
   *A61L 27/54* (2006.01)
   *A61L 27/58* (2006.01)
   *A61K 47/34* (2017.01)
   *A61K 9/14* (2006.01)
   *A61F 9/00* (2006.01)
   *A61F 9/007* (2006.01)

(52) U.S. Cl.
   CPC ............ *A61K 31/381* (2013.01); *A61K 47/34* (2013.01); *A61L 27/18* (2013.01); *A61L 27/54* (2013.01); *A61L 27/58* (2013.01); *A61F 9/0017* (2013.01); *A61F 9/00781* (2013.01); *A61L 2430/16* (2013.01)

(56) References Cited

U.S. PATENT DOCUMENTS

| | | |
|---|---|---|
| 5,834,498 A | 11/1998 | Burk |
| 6,124,344 A * | 9/2000 | Burk .................. A61K 31/557 514/438 |
| 6,602,900 B2 | 8/2003 | Burk |
| 2004/0054374 A1 | 3/2004 | Weber et al. |
| 2007/0099984 A1 | 5/2007 | Burk et al. |
| 2008/0145403 A1 | 6/2008 | Spada |
| 2008/0292679 A1 * | 11/2008 | Lyons ................. A61F 9/0017 424/428 |
| 2010/0278897 A1 | 11/2010 | Shi et al. |

FOREIGN PATENT DOCUMENTS

| | | |
|---|---|---|
| WO | 1999-025358 | 5/1999 |
| WO | 2011-091205 | 7/2011 |

OTHER PUBLICATIONS

Schuster, Victor et al, Synthetic Modification of Prostaglandin F2α Indicates Different Structural Determinants of Binding to the Prostaglandin F Receptor Versus the Prostaglandin Transporter, Molecular Pharmacology, 2000, 1511-1516, 58.

United States Pharmacopeia, The National Formulary, USP23, 1995, 1790-1798, 18.

Woodward, David et al, Identification of an antagonist that selectively blocks the activity of (prostamides prostaglandin-ethanolamides) in the feline iris, British Journal of Pharmacology, 2007, 342-352, 150.

* cited by examiner

PROSTAMIDE-CONTAINING INTRAOCULAR IMPLANT

CROSS-REFERENCE

This application is a continuation of U.S. patent application Ser. No. 14/211,265, filed on Mar. 14, 2014, which claims priority under 35 U.S.C. §119 (e) from U.S. Provisional Application Ser. No. 61/798,291, filed on Mar. 15, 2013, U.S. Provisional Application Ser. No. 61/877,573, filed on Sep. 13, 2013, and U.S. Provisional Application Ser. No. 61/898,210, filed on Oct. 31, 2013, which are hereby incorporated by reference in their entirety.

BACKGROUND

The present invention generally relates to devices and methods to treat an eye of a patient, and more specifically to intraocular implants that provide extended release of a therapeutic agent to an eye in which the implant is placed to treat ocular hypertension, such as by reducing or at least maintaining intraocular pressure (IOP), and to methods of making and using such implants.

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye often characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The increased intraocular tension in glaucoma is due to the obstruction of aqueous humor outflow. In chronic open-angle glaucoma, the anterior chamber and its anatomic structures appear essentially normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Reduction of intraocular pressure may help to prevent glaucoma or loss of vision due to glaucoma. Currently, eye drops containing therapeutically active agents for reducing intraocular pressure are given to many patients, who may take the drops one or more times a day to reduce elevated intraocular pressure associated with glaucoma.

It would be advantageous to provide eye implantable drug delivery systems, such as intraocular implants, and methods of using such systems, that are capable of releasing a therapeutic agent, such as a hypotensive (or IOP-lowering) agent, at a sustained or controlled rate for extended periods of time and in amounts with few or absent negative side effects to thereby reduce intraocular pressure in an eye of a patient, including but not limited to patients suffering from or at risk of developing glaucoma.

SUMMARY

Extended, long term reduction of intraocular pressure in the eye may be provided by intraocular administration of one or more of the biodegradable intraocular implants described herein. A biodegradable intraocular implant according to the present disclosure comprises or consists of a biodegradable polymer material and a therapeutic agent associated with the biodegradable polymer material. The implant(s) can be administered to the eye as monotherapy and may provide the therapeutic agent directly to an ocular region of the eye in an amount effective for reducing elevated intraocular pressure (ocular hypertension) in the eye for an extended period, such as, for example, for 1-6 months or more. The implants may also be used to treat or prevent glaucoma or other medical conditions of the eye associated with elevated intraocular pressure.

The therapeutic agent contained by the intraocular implant of the present disclosure may comprise, consist essentially of, or consist of, a compound that is effective in reducing intraocular pressure in a hypertensive eye. In some embodiments the therapeutic agent comprises or consists of a compound having Formula I, or a pharmaceutically acceptable salt or ester prodrug thereof,

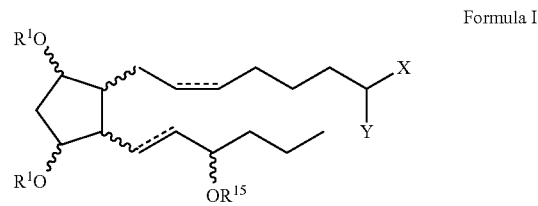

Formula I wherein the wavy segments represent an α or β bond, dashed lines represent a double bond or a single bond, R is a substituted heteroaryl radical, wherein each $R^1$ is independently selected from the group consisting of hydrogen and a lower alkyl radical having up to six carbon atoms, X is $-OR^1$, $-N(R^1)_2$, or $-N(R^5)SO_2R^6$, wherein $R^5$ represents hydrogen or $CH_2OR^6$, $R^6$ represents hydrogen, a lower alkyl radical having up to six carbon atoms, a halogen substituted derivative of said lower alkyl radical, or a fluoro substituted derivative of said lower alkyl radical, and $R^{15}$ is hydrogen or a lower alkyl radical having up to six carbon atoms; and Y is =O or represents 2 hydrogen radicals.

The substituent(s) on the substituted heteroaryl radical in Formula I may be selected from the group consisting of $C_1$ to $C_6$ alkyls; halogens (such as fluoro, chloro, and bromo); trifluoromethyl ($CF_3$); $COR^1$ (such as $COCH_3$); $COCF_3$; $SO_2N(R^1)_2$ (such as $SO_2NH_2$); $NO_2$; and CN.

In more specific embodiments the therapeutic agent may comprise or consist of a compound having Formula II, or a pharmaceutically acceptable salt or ester prodrug thereof, Formula II

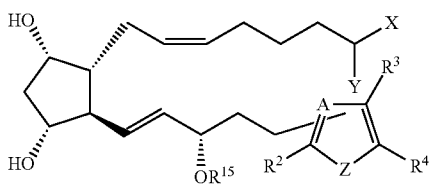

wherein $R^1$, X, Y, $R^5$, $R^6$, and $R^{15}$ are all as defined above for Formula I, and wherein Z is selected from the group consisting of O and S, A is selected from the group consisting of N, —CH, and C, $R^2$ is selected from the group consisting of hydrogen, halogen, and a lower alkyl having from 1 to 6 carbon atoms, $R^3$ and $R^4$ are independently selected from the group consisting of hydrogen, halogen, a lower alkyl having from 1 to 6 carbon atoms, or, together with

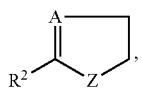

$R^3$ and $R^4$ forms a condensed aryl ring.

In some embodiments the therapeutic agent contained by the implant of the present disclosure comprises or consists of a compound having Formula II, wherein at least one of $R^2$, $R^3$ or $R^4$ is independently selected from the group consisting of chloro, bromo, and $C_1$-$C_6$ alkyl. In more specific embodiments at least one of $R^2$, $R^3$ or $R^4$ is chloro or bromo. In more specific embodiments at least one of $R^2$, $R^3$ or $R^4$ is bromo. In a more specific embodiment at least two of $R^2$, $R^3$ or $R^4$ are chloro. In some embodiments the therapeutic agent comprises or consists of a compound having Formula II, wherein at least one of $R^2$, $R^3$ or $R^4$ is ethyl, propyl, or butyl. In some embodiments, $R^6$ is methyl, ethyl or trifluoromethyl. In one embodiment the therapeutic agent comprises or consists of a compound having Formula II, wherein $R^{15}$ is hydrogen or methyl.

In one embodiment the therapeutic agent comprises or consists of a compound having Formula II, wherein X is —N($R^1$)$_2$ and Y is =O.

In one embodiment the therapeutic agent contained by the implant of the present disclosure comprises or consists of a compound having Formula III Formula III

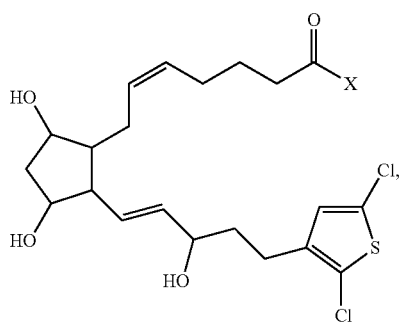

or a pharmaceutically acceptable salt or ester prodrug thereof, wherein X is —OH or —N($R^1$)$_2$, and wherein $R^1$ is independently selected from the group consisting of hydrogen and $C_1$-$C_6$ alkyl.

In a further embodiment the therapeutic agent comprises or consists of a compound having Formula IV Formula IV

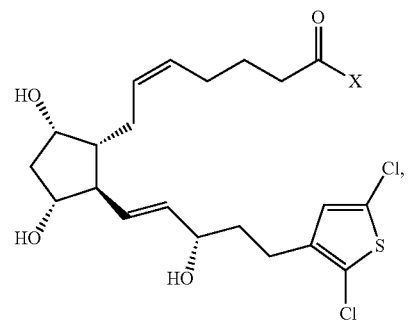

or a pharmaceutically acceptable salt or ester prodrug thereof, wherein X is —OH or —N($R^1$), and wherein $R^1$ is independently selected from the group consisting of hydrogen and a $C_1$-$C_6$ alkyl.

In a specific embodiment the therapeutic agent comprises or consists of a compound having Formula IV wherein X is —NH$_2$. This compound is referred to herein as Compound 1 and has the following structure:

Compound 1

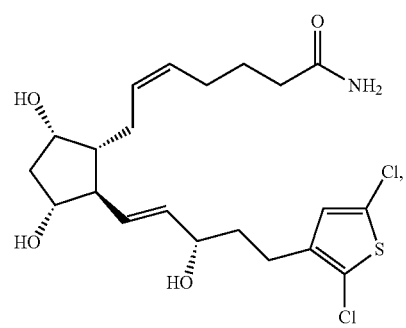

In another embodiment the therapeutic agent comprises or consists of a compound having Formula IV, or a pharmaceutically acceptable salt thereof, wherein X is —OH. This compound is referred to herein as Compound 2 and has the following structure:

Compound 2

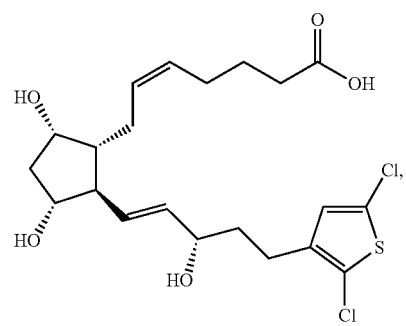

It will be readily apparent to those skilled in the art that Formulas I-IV contain one or more stereocenters. Unless it is specifically noted otherwise, the scope of the present invention includes all enantiomers and diastereomers of Formulas I-IV and racemic mixtures thereof. Some Compounds having any one of Formulas I-IV may form salts with pharmaceutically acceptable acids or bases, and such pharmaceutically acceptable salts of the compounds are also within the scope of the invention.

Accordingly, the present invention provides for a biodegradable intraocular implant effective for reducing intraocular pressure in an eye of a patient, wherein the implant comprises or consists of a biodegradable polymer material and a Compound having Formula I, II, III, or IV, as defined above, or a pharmaceutically acceptable salt thereof. Specific embodiments provide for a biodegradable intraocular implant comprising or consisting of a biodegradable polymer material and Compound 1 or Compound 2, or a mixture thereof, associated with the biodegradable polymer material.

Another embodiment is a biodegradable intraocular implant comprising a biodegradable polymer material and Compound 1 as the pharmaceutically active agent, wherein the intraocular implant comprises no pharmaceutically active agent or IOP-lowering agent other than Compound 1.

Compounds having any of Formulas I-IV may be prepared by methods known in the art. For example, see U.S. Pat. Nos. 6,602,900, 6,124,344, 5,741,810, and 5,834,498.

The Compound having Formula I, II, III, or IV may be associated with the biodegradable polymer material. Thus, the Compound may be mixed with, dissolved and/or dispersed within, encapsulated by, or coupled to the biodegradable polymer material. The Compound having Formula I, II, III, or IV may be uniformly or non-uniformly dispersed within or distributed throughout the biodegradable polymer material. Release of the Compound from an implant following placement in an eye may occur by diffusion of the Compound, erosion or degradation of the polymer material, dissolution, osmosis, or any combination thereof.

The biodegradable intraocular implant, described herein may be specifically sized and formulated for placement in an ocular region of an eye, such as, for example, the vitreous body or anterior chamber of the eye, to treat glaucoma and reduce intraocular pressure, including, for example, elevated intraocular pressure (or ocular hypertension) in the eye.

Specific embodiments provide for an intraocular biodegradable implant that will release a Compound having any of Formulas I-IV (such as for example Compound 1) continuously in vitro and/or in vivo in an eye for 1-3 months, 3 months or more, for 3-6 months, or for 6 months or more after placement in the eye of a patient.

An intraocular implant according to the present disclosure may release 5 to 200 nanograms (ng) of the Compound per day, 10 to 200 nanograms of the Compound per day, 5 to 100 nanograms of the Compound per day, 10 to 100 nanograms of the Compound per day, 10 to 50 nanograms of the Compound per day, at least 10 ng but not more than 50 ng of the Compound per day, from 10 to about 35 ng of the Compound per day, or from 20 to 35 nanograms of the Compound per day for 1 month or more, 2 months or more, 1-3 months, for 3-6 months, or for 6 months or more.

Implants of the present invention are designed to release a Compound of Formula IV, such as for example Compound 1, in a controlled fashion. In some forms, the implant will provide a linear or near constant rate of release of the Compound for 1 month or more, e.g. for 1, 3, or 6 months.

Daily dosages of Compound 1 in the range of 5-200, 10-100 nanograms, or even 5-50 nanograms, when delivered or released directly into the anterior chamber, may be a therapeutically effective amount for reducing intraocular pressure in an eye. The term "therapeutically effective amount" or "effective amount" refers to the level or amount of active agent (e.g., Compound 1 or Compound 2) needed to reduce intraocular pressure without causing significant negative or adverse side effects to the eye or a region of the eye to which the agent is administered.

Implants of the present invention may reduce intraocular pressure in an eye in a patient for 1 month (30 days) or more, 1 to 3 months, 3 months, 3-6 months, or even 6 months or more after placement of the implant in the eye. The patient is typically a human or non-human mammal that is experiencing or diagnosed with elevated intraocular pressure or ocular hypertension in one or both eyes. The patient may be further defined as one suffering from glaucoma, since glaucoma frequently includes elevated intraocular pressure. Accordingly, the implants described herein may be used generally to reduce elevated intraocular pressure in an eye and to treat glaucoma in a patient. In this regard, one embodiment is a method of reducing ocular hypertension or elevated intraocular pressure in a patient in need thereof, the method comprising placing a biodegradable intraocular implant according to the present disclosure in an eye of the patient.

In particular forms of the treatment method, one or more intraocular implants comprising a Compound having any of Formulas I-IV may be placed, or more specifically injected, into the anterior chamber of an eye to thereby reduce intraocular pressure and ocular hypertension in the eye. Accordingly, the intraocular implant may, for example, be sized and formulated for placement in the anterior chamber the eye. Such implants may be referred to as "intracameral" implants.

Implants of the present disclosure are designed to provide long lasting relief from elevated intraocular pressure (or ocular hypertension) by providing a sustained, continuous release of a therapeutically effective amount of Compound 1 (or more generally a Compound having Formula I, II, III, or IV), or any pharmaceutically acceptable salt thereof, directly into the affected region of the eye, such as the anterior chamber of the eye. In this context, a therapeutically effective amount of Compound 1 may be a dosage of between 5 to 200 ng/day, 10 to 200 ng per day, 5 to 50 ng/day, or more specifically 10-40 ng/day, or even more specifically about 15 ng/day, 20 ng/day, or 30 ng/day. The patient may be a human or non-human mammal in need of treatment for ocular hypertension (elevated intraocular pressure) or glaucoma. The implant may be in the form of an extruded filament or compressed tablet. Other forms may include wafers, films, or sheets. The extruded filament can be a cylindrical or non-cylindrical rod having a diameter and cut to a length suitable for placement in the eye, such as the anterior chamber or vitreous body of the eye.

One embodiment is an extruded, intracameral, biodegradable implant comprising about 8% by weight Compound 1 and from 0.001% to 10% by weight hexadecane-1-ol (hexadecanol), wherein the implant has a total mass of from 30 to 100 µg and that releases between 10 and 50 ng of Compound 1 per day for 3 to 5 months in vitro in phosphate buffered saline at 37° C. In some forms of this implant, the biodegradable polymer material comprises a poly(D,L-lactide) having an acid end group and an inherent viscosity of 0.16-024 dl/g, and a poly(D,L-lactide) having an ester end group and an inherent viscosity of 0.25-0.35 dl/g, and a poly(D,L-lactide-co-glycolide) copolymer having an ester end group, a D,L-lactide to glycolide molar ratio of about 75:25 (e.g., from 73:27 to 77:23), and an inherent viscosity of 0.16-0.24 dl/g, wherein the inherent viscosity of each polymer and copolymer is measured for a 0.1% solution of the polymer or copolymer in chloroform at 25° C.

Patients that may be effectively treated with a biodegradable intracameral implant comprising a Compound having I, II, III, or IV (for example Compound 1) may include those having, suffering from, or diagnosed with glaucoma, open-angle glaucoma, closed-angle glaucoma, chronic angle-closure glaucoma, patent iridotomy, ocular hypertension, elevated intraocular pressure, pseudoexfoliative glaucoma, or pigmentary glaucoma. An implant according to this disclosure may be effective for reducing intraocular pressure in an eye that has low, normal, or elevated intraocular pressure. Therefore, an implant according to this disclosure may be effective for treating glaucoma in all its forms, including glaucoma characterized by elevated intraocular pressure, as well as low-tension or normal-tension glaucoma, since these patients, too, may potentially benefit from a further reduction in intraocular pressure. Because of their ability to release therapeutically effective amounts of a potent intraocular pressure-reducing agent, such as Compound 1, for sustained periods, implants of the instant invention are expected to be capable of reducing intraocular pressure in these patients for long periods without the need for frequent intraocular injections or regular instillation of eye drops to the ocular surface as may be necessary with topical therapy. Moreover, the greater potency of Compound 1 for lowering IOP relative to some other prostamides and anti-glaucoma agents makes it possible to produce smaller implants with longer administration periods that are safer and better for the eye and therefore the patient.

Thus, one embodiment of the present invention is a method for reducing intraocular pressure (IOP) in an eye, the method comprising placing a biodegradable intraocular implant in the eye, the implant comprising or consisting of a biodegradable polymer material and a Compound having any of Formulas I-IV, or a pharmaceutically acceptable salt thereof, associated with the polymer material, wherein the implant reduces intraocular pressure in the eye for 1, 3, or 6 months or more after placement in the eye. In some instances the implant may reduce IOP in the eye by at least 30% relative to the IOP in the eye without the implant or before receiving the implant (baseline IOP) for 1, 3, or 6 months or more. The implant may be placed in an ocular region of the eye and may, therefore, be sized for placement in an ocular region of the eye. The patient may have low or normal intraocular pressure or may be suffering from elevated intraocular pressure, sometimes referred to as ocular hypertension, or the patient may have glaucoma. In a more specific form, the patient is suffering from or diagnosed with glaucoma or elevated intraocular pressure and the implant is placed in the anterior chamber or vitreous body of the affected eye(s). In a specific embodiment the implant is placed in the anterior chamber angle (or iridocorneal angle), and even more specifically in the inferior iridocorneal angle, of the affected eye(s). In any of these methods, the Compound in the implant (i.e., the therapeutic agent) may comprise or consist of Compound 1 or Compound 2, a pharmaceutically acceptable salt of Compound 1 or 2, or any mixture thereof, and the implant may be placed in the anterior chamber or vitreous body of the eye via intracameral or intravitreal injection. In specific embodiments the implant is placed in the anterior chamber angle (or iridocorneal angle) of the eye. The implant may also be placed in the subconjunctival region of the eye.

Accordingly, the disclosure provides for a method of treating glaucoma in a patient, comprising the step of placing a biodegradable intraocular implant as described herein in an eye of the patient. The implant may be placed in the anterior chamber of the eye or other ocular region of the eye, to thereby treat the glaucoma.

Some embodiments include a method of administering a Compound having Formula III or IV, such as Compound 1 or Compound 2, without eye drops, the method comprising inserting an implant described herein into an eye of a patient in need thereof. The implant is preferably placed in the anterior chamber of the eye.

One embodiment provides for a method of reducing intraocular pressure in a patient in need thereof comprising administering to the eye(s) of the patient a pharmaceutical composition, the composition comprising a therapeutically effective amount of a compound having Formula I, II, III, or IV. Some embodiments provide for a method of reducing intraocular pressure in a patient in need thereof comprising administering to the eye(s) of the patient a pharmaceutical composition comprising a therapeutically effective amount of Compounds 1 or 2. The pharmaceutical composition for reducing intraocular pressure will generally be biocompatible with the eye and will contain a therapeutically effective amount of the Compound and a pharmaceutically acceptable excipient. Biocompatible implants and polymers produce few or no toxic effects, are not injurious or physiologically reactive, and do not cause an immunological reaction. In a specific embodiment the pharmaceutical composition is in the form of a liquid, such as an aqueous solution, oil, or emulsion. In one embodiment the pharmaceutical composition is administered to the patient's eye(s) topically. For example, the pharmaceutical composition may be administered by eye drops. In another embodiment, the pharmaceutical composition is administered to the anterior chamber of the eye without using eye drops.

Pharmaceutical compositions may be prepared by combining a therapeutically effective amount of at least one compound according to the present invention, or a pharmaceutically acceptable salt thereof, as an active agent, with conventional pharmaceutically acceptable excipients, and by preparation of unit dosage forms suitable for topical ocular use. The therapeutically effective amount may be between 0.0001 and 5% or 10% (w/v) in liquid formulations. For ophthalmic application, physiological saline solution may be one possible vehicle. The pH of such compositions should preferably be maintained between 6.5 and 7.2 with an appropriate buffering agent or system, a substantially neutral pH being preferred. The formulations may also contain one or more conventional, pharmaceutically acceptable preservatives, stabilizers, antioxidants, chelating agents, tonicity agents (e.g. alkaline metal or alkaline earth salts), and surfactants. Certain compositions may include both a buffer component and a tonicity component.

Other embodiments provide for a method of making biodegradable intraocular implants effective for reducing intraocular pressure in a patient, the implant comprising or consisting of a therapeutic agent, a biodegradable polymer material, and, optionally, one or more excipients, the method comprising in order a) blending the therapeutic agent with a biodegradable polymer or two or more biodegradable polymers and one or more excipients, if any, to form a mixture, b) extruding the mixture to form a filament, and c) cutting the filament to lengths suitable for placement in an eye of a patient suffering from elevated intraocular, thereby forming the intraocular implants. In particular embodiments the filament is cut to lengths suitable for placement in the anterior chamber of an eye. The therapeutic agent may comprise a compound having any one of Formulas I-IV or may comprise Compounds 1 or 2, as defined herein. In some instances the therapeutic agent used for blending with the polymer(s) (step a) may be in the form of a solid. The mixture may be extruded at a temperature of from 60° C. to 150° C.

Yet other embodiments provide for an apparatus for implanting or injecting a biodegradable intraocular implant, according to any of the embodiments described herein, into an ocular region of an eye in a patient suffering from glaucoma or ocular hypertension (i.e., elevated intraocular pressure), the apparatus comprising an elongate housing having a longitudinal axis and a cannula extending longitudinally from the housing, the cannula having a lumen extending therethrough, the lumen configured to receive an intraocular implant, the apparatus further comprising an intraocular implant according to any of the embodiments described herein. The implant may be located within the cannula lumen or in a position proximal to the cannula lumen. In specific forms of the apparatus the dimensions of the cannula are identical to that or not greater than that of a 21, 22, 25, 27, 28, or 30 gauge needle and the cannula will have a beveled or sharp tip to facilitate the penetration of ocular tissue. In some forms, the outer and inner diameters of the cannula are not greater than those of a 25 or 27 gauge needle.

Also within the scope of this invention are methods for delivering the intraocular implant into the eye of a patient suffering from glaucoma or elevated intraocular pressure using an apparatus as described above, the apparatus comprising a cannula having a proximal end, a distal sharp end, and a lumen extending therethrough, an intraocular implant selected from any of those described herein, and an actuator, the movement of which causes the implant to be ejected from the apparatus, the cannula lumen sized to receive the intraocular implant and permit translation of the implant therethrough, the method comprising the steps of inserting the cannula into an ocular region of a patient's eye, and depressing or activating the actuator, thereby ejecting the implant from the cannula into the patient's eye. In some embodiments the ocular region of the eye into which the implant is injected can be the anterior chamber or vitreous body of the eye.

DETAILED DESCRIPTION

Definitions

Figure 1:
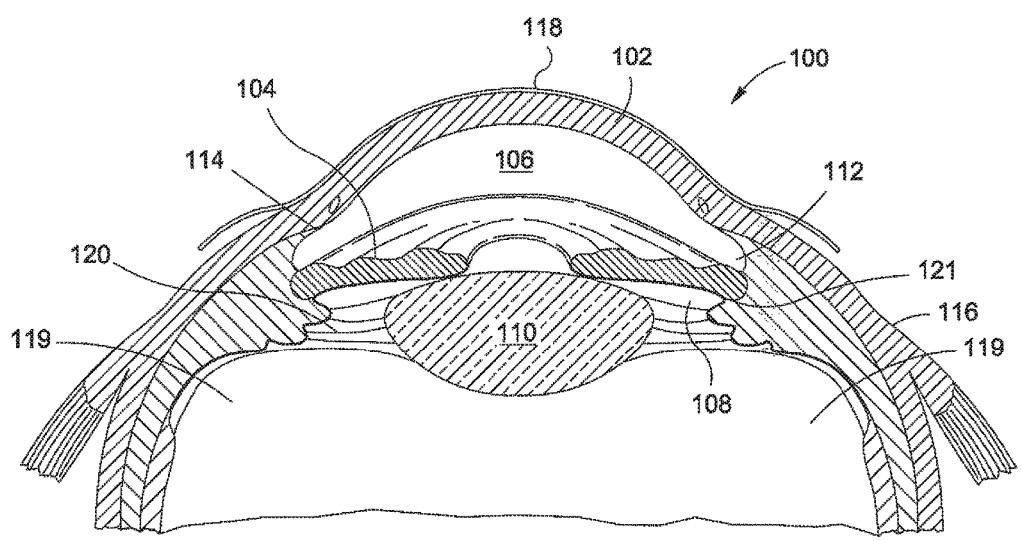
FIG. 1 shows a cross-section of the mammalian eye.

"$C_1$-$C_6$ alkyl" means an alkyl having 1 to 6 carbon atoms.

The symbol "H", as used in the Formulas herein, represents a hydrogen atom.

The symbol "O", as used in the Formulas herein, represents an oxygen atom.

The symbol "N", as used in the Formulas herein, represents a nitrogen atom.

The symbol "S", as used in the Formulas herein, represents a sulfur atom.

The symbol "C", as used in the Formulas herein, represents a carbon atom.

The symbol "Cl", as used in the Formulas herein, represents a chlorine atom.

The symbol "Br", as used in the Formulas herein, represents a bromine atom.

"Cumulative release profile" refers to the cumulative total percent of an active agent (such as, for example, Compound 1) released from an implant into an ocular region in vivo over time or into a specific release medium (e.g, PBS) in vitro over time.

A "prodrug" means a compound (e.g., a drug precursor) that is transformed in vivo to yield an active form of the compound. The transformation may occur by various mechanisms (e.g., by metabolic or chemical processes), such as, for example, through hydrolysis.

The term "pharmaceutically acceptable salts" refers to salts or complexes that retain the desired biological activity of the Compound or therapeutic agent and exhibit minimal or no undesired toxicological effects to the mammal or cell system to which they are administered.

An "intraocular implant" refers to a device or element that is configured to be placed in the eye. Examples include extruded filaments, comprising a biodegradable polymer material and a pharmaceutically active agent, such as a Compound having Formula I, II, III, or IV associated with the polymer material, and cut to a length suitable for placement in an eye. Intraocular implants are generally biocompatible with the physiological conditions of an eye and do not cause adverse reactions in the eye. In certain forms of the present invention, an intraocular implant may be sized and formulated for placement in the anterior chamber or vitreous body of the eye. Intraocular implants may be placed in an eye without significantly disrupting vision of the eye. Intraocular implants comprising one or more biodegradable polymers and a Compound having Formula I, II, III, or IV or a pharmaceutically acceptable salt thereof are examples of an intraocular implant (drug delivery system) within the scope of the present invention.

An "intracameral" implant is an intraocular implant that is sized and formulated for placement in the anterior chamber of the eye. Non-limiting examples include Implants 1-4 and 9-11 described in Table 2.

An "intravitreal" implant is an intraocular implant that is sized and formulated for placement in the vitreous body of the eye.

"Suitable for or configured for, sized for, or structured for insertion, implantation, or placement in (or into) an ocular region or site" with regard to an implant, means an implant which has a size (e.g., dimensions and weight) such that it can be inserted, implanted, or placed in an ocular region such as the anterior chamber or vitreous body of the eye without causing excessive tissue damage or significantly impairing the existing vision of the patient into which the implant is implanted or inserted.

"Treating" and "treatment" as used herein includes any beneficial effect in the eye of a patient produced by the present methods. Treatment of an ocular condition, such as ocular hypertension or elevated intraocular pressure, or glaucoma, may reduce or resolve the ocular condition or may reduce or retard the progression of one or more signs, symptoms, or risk factors of or associated with the ocular condition. The sign(s) or symptom(s) positively affected by the treatment will depend on the particular condition. Examples of beneficial (and therefore positive) effects produced by the present methods may include a reduction in intraocular pressure, ocular pain (i.e., eye pain), ocular swelling, and/or ocular inflammation. Treatment by any of the methods described herein using one or more of the intraocular implants described herein may, in some instances, also improve the general well being, comfort, and/or visual performance of the eye.

"Active agent", "drug", "therapeutic agent," "therapeutically active agent," and "pharmaceutically active agent" refer to the chemical compound, or drug substance, that produces a desired therapeutic effect in the eye of the patient (human or non-human mammal) to which it is administered and that treats the ocular condition (medical condition of the eye), such as elevated intraocular pressure (ocular hypertension) or glaucoma, affecting the patient. One non-limiting example of a therapeutically (or pharmaceutically) active agent or therapeutic agent in the context of the present invention is Compound 1.

A "patient" can be a human or non-human mammal in need of treatment.

The "eye" is the sense organ for sight, and includes the eyeball, or globe, the orbital sense organ that receives light and transmits visual information to the central nervous system. Broadly speaking the eye includes the eyeball and the ocular regions, tissues, and fluids which constitute the eyeball, the periocular muscles (such as the oblique and rectus muscles) and the portion of the optic nerve which is within or adjacent to the eyeball.

The term "therapeutically effective amount" or "effective amount" refers to the level or amount of active agent needed to treat an ocular condition without causing significant negative or adverse side effects to the eye or a region of the eye to which the agent is administered.

The term "biodegradable polymer" refers to a polymer or polymers which degrade in vivo, and wherein degradation of the polymer or polymers over time occurs concurrent with or subsequent to release of the therapeutic agent. A biodegradable polymer may be a homopolymer, a copolymer, or a polymer comprising more than two different structural repeating units.

The term "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of an ocular region in an eye include the anterior chamber, the posterior chamber, the vitreous cavity (vitreous body or the vitreous), the choroid, the suprachoroidal space, the conjunctiva, the subconjunctival space, the sub-Tenon space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site. Glaucoma can be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. Glaucoma can also be considered a posterior ocular condition because the therapeutic goal is to prevent the loss of or reduce the occurrence of loss of vision due to damage to or loss of retinal cells or optic nerve cells (i.e. neuroprotection).

Pharmaceutical Compositions for Topical Application to an Eye

For topical application (e.g. in the form of eye drops), pharmaceutical compositions may be prepared by combining a therapeutically effective amount of at least one compound according to the present invention, or a pharmaceutically acceptable salt thereof, as an active agent, with one or more pharmaceutically acceptable excipients, and by preparation of unit dosage forms suitable for topical ocular use. A therapeutically efficient amount may be between 0.0001 and 10% (w/v), or from 0.001 to 5.0% (w/v) in liquid formulations.

Preferably solutions are prepared using a physiological saline solution as a major vehicle. The pH of such ophthalmic solutions should preferably be maintained between 6.5 and 7.2 with an appropriate buffer system, a substantially neutral pH being preferred. The compositions may also contain conventional, pharmaceutically acceptable preservatives, buffers, tonicity agents, antioxidants, stabilizers, and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity agents may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Acceptable antioxidants may include sodium metabisulfite, sodium thiosulfate, acetylcysteine, butylated hydroxyanisole and butylated hydroxytoluene.

Other excipients may include one or more chelating agents.

The pharmaceutical compositions for topical use may be conveniently packaged in forms suitable for metered application, such as in containers equipped with a dropper, to facilitate application to the eye.

Size and Configuration of the Biodegradable Intraocular Implant

Biodegradable implants that are sized and formulated for placement in the eye of a patient (intraocular implants) and that comprise a Compound having any of Formulas I-IV, dispersed in a biodegradable polymer material (or matrix) may be useful for reducing intraocular pressure and treating glaucoma. We have discovered here that Compound 1 is particularly effective for reducing intraocular pressure in an eye when administered directly into the anterior chamber of the eye. Biodegradable implants are a safe, non-toxic, and effective means by which to administer this compound to the anterior chamber.

Consistent with this preferred site of delivery, implants of this invention are sized and formulated to be received in the anterior chamber of the eye (e.g., a human eye), and preferably within the anterior chamber angle of the eye, with little or no adverse effects on the eye, particularly the corneal endothelium, and without obstructing or significantly impairing the vision of the patient. Patients receiving the implant will receive a therapeutically effective amount of the Compound (which in some embodiments is Compound 1) and will preferably experience little or no hyperemia or inflammation in the eye following placement of the implant in the eye. In this regard, then, the invention discloses intraocular implants that are sized and formulated for placement in the anterior chamber of the eye, that are biocompatible with the eye, causing little or no immunological reaction or inflammation in the eye, and that may be effective for reducing intraocular pressure in an eye for at least one month, such as, for example, for 1 to 6 months or longer. The exceptional potency of Compound 1 for lowering IOP, for example, makes it possible to reduce the size of the intraocular implant needed to deliver a therapeutically effective dose of the IOP-lowering agent to target tissues and sites in the eye such as the anterior chamber, possibly minimizing potential irritation or injury to the tissues in the eye and more generally providing increased safety and greater overall benefit and comfort for the patient. Moreover, the use of smaller implants may reduce the time needed to completely degrade the implant in the eye following drug release.

An implant may have a size suitable for insertion, placement or implantation in an ocular region or site, such as the anterior chamber, posterior chamber, or vitreous body of the eye. The size of an implant may affect the rate of release, period of treatment, and concentration of the Compound having one of Formulas I-IV in treated tissue. At equal active agent loads, larger implants may deliver a proportionately larger dose.

An implant sized for placement in the anterior chamber (an intracameral implant) will generally have a diameter (or other dimension as appropriate for non-cylindrical filaments) of from 100 to 400 µm and a length of from 0.5 to 6 mm. The implants may generally be formed by a single or double extrusion process, may be cylindrical or non-cylindrical, and may have a total weight ranging from 10 µg to 500 µg. The weight may depend, in part, on the dosage desired. In some embodiments, implants suitable for placement in the anterior chamber of an eye and suitable for use according to the invention will have a diameter of between 100 µm and 300 µm, a length of between 0.5 mm and 2 mm, and a total weight of between 10 µg and 200 µg or between 10 µg and 100 µg. In some instances, the intracameral implant for reducing IOP has a total weight of from 10 µg to 100 µg, or more specifically from 30-100 µg. One embodiment is an extruded biodegradable intraocular implant that is suitable for placement in the anterior chamber of an eye and that is about 200 µm in diameter and about 1.5 mm in length.

The eye(s) in some patients suffering from glaucoma or more generally ocular hypertension may be more receptive to placement of the biodegradable implant in the vitreous body of the eye. The vitreous body may accept larger implants of the same general formulation. For example, an intravitreal implant may have a length of 1 mm to 10 mm, a diameter of 0.5 mm to 1.5 mm, and a total weight of 50 µg to 5000 µg. The implant may be scaled up or down depending on the site of administration in the eye and the size or the vitreous volume of the patient. While in most cases a single implant may be found to reduce intraocular pressure in an eye for a sustained period (e.g., at least 3 months), in some instances, the practitioner may find it useful to place two or more of the presently described implants in an ocular region of the eye to improve the therapeutic effect.

Regarding configuration, intraocular implants may be in the form of extruded rods or in the form of non-cylindrical filaments, having the dimensions described above. Wafers, sheets, or films and in some cases compressed tablets may also find use according to the present invention.

Biodegradable Polymer Material

In general, an implant according to the present invention will comprise or consist of a biodegradable polymer material and a Compound having any one of Formulas I-IV associated with the biodegradable polymer material. The polymer material may comprise or consist of one, two, three, or more biodegradable polymers, and optionally one or more excipients to further improve the stability and/or release characteristics of the implant.

Examples of useful biodegradable polymers include polylactide polymers and poly(lactide-co-glycolide) copolymers. In some embodiments, the biodegradable polymer material may comprise a polylactide, a poly(lactide-co-glycolide), a mixture of two or more polylactide polymers (e.g., first and second polylactide polymers), a mixture of two or more poly(lactide-co-glycolide) copolymers, or a mixture of polylactide and poly(lactide-co-glycolide) polymers In particular forms of any of these implants, the polylactide polymer may be a poly(D,L-lactide) and the poly(lactide-co-glycolide) copolymer may be a poly(D,L-lactide-co-glycolide). In any of the aforementioned combinations, the two or more polymers may differ, one from the other, on the basis of their end group, repeating unit, inherent viscosity, or any combination thereof. Polylactide and poly(lactide-co-glycolide) polymers used in the present implants may have either a carboxyl (—COOH) or ester end group. In addition, two or more poly(lactide-co-glycolide) polymers may differ one from the other by the lactide:glycolide ratio in each polymer, which may vary from about 85:15 to about 50:50 to about 75:25, depending on the polymer.

Poly(D,L-lactide) or PLA may be identified by CAS Number 26680-10-4 and may be represented as:

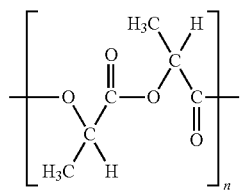

Poly(D,L-lactide-co-glycolide) or PLGA may be identified by CAS Number 26780-50-7 and may be represented as:

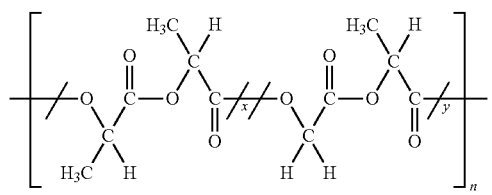

wherein x is the number of D,L-lactide repeat units and y is the number of glycolide repeat units, and n is the number of D,L-lactide-co-glycolide repeat units. Thus, poly(D,L-lactide-co-glycolide) (or PLGA) comprises one or more blocks of D,L-lactide repeat units and one or more blocks of glycolide repeat units, where the size and number of the respective blocks may vary.

The molar percent of each monomer or repeat unit in a PLGA copolymer may be 0-100%, about 15-85%, about 25-75%, or about 35-65%. In some embodiments, the D,L-lactide may be about 50% to about 75%, about 48% to about 52%, or about 50%; about 73% to about 77%, or about 75% of the PLGA polymer on a molar basis. The balance of the polymer may essentially be glycolide repeat units. For example, glycolide may be about 25% to about 50%, about 23% to about 27%, or about 25%; about 48% to about 52%, or about 50% of the PLGA polymer on a molar basis. Other groups, such as terminal or capping groups (end group) may be present in small amounts. As described above, in some embodiments, PLGA copolymers are used in conjunction with PLA polymers. In some implants, a 75/25 PLGA polymer having an ester end group is used.

The hydrophilic or hydrophobic character of the end groups may be useful in varying polymer material degradation. Polymers with a hydrophilic end group may degrade faster than polymers with a hydrophobic end group because a hydrophilic group may take up water. Examples of suitable hydrophilic end groups include, but are not limited to, carboxyl (acid end group), hydroxyl, and polyethylene glycol. These groups may be introduced by using an appropriate initiator. End groups may also be introduced after polymerization is complete to convert the terminal hydroxyl groups into other end groups. For example, ethylene oxide may convert hydroxyl to polyethylene glycol. Hydrophobic ended (also referred to as capped or end-capped) polymers have an ester linkage hydrophobic in nature at the polymer terminus.

Other polymers of interest include or may be selected from hydroxyaliphatic carboxylic acids, either homopolymers or copolymers, hyaluronic acid, sodium hyaluronate, polycaprolactones, polysaccharides, polyethers, calcium alginate, celluloses, carboxymethyl cellulose, polyvinyl alcohol, polyesters and combinations thereof.

Useful polysaccharides may include, without limitation, calcium alginate, and functionalized celluloses, such as carboxymethylcellulose esters characterized by being water insoluble, and having a molecular weight of about 5 kD to 500 kD, for example.

Release of a drug from a biodegradable polymer material is the consequence of several mechanisms or combinations of mechanisms. Some of these mechanisms include desorption from the implant's surface, dissolution, diffusion through porous channels of the hydrated polymer and erosion of the polymer(s) that make up the matrix. Erosion can be bulk or surface or a combination of both. The polymer matrix may release the therapeutic agent at a rate effective to sustain release of an amount of the agent (for example, Compound 1) for more than one month, for 1-3 months, for 3-6 months, or for 6 months after implantation into an eye. For example, an implant may comprise Compound 1, and the polymer material (or matrix) of the implant may degrade at a rate effective to sustain release of a therapeutically effective amount of Compound 1 for one, two, three, or 6 month(s) in vitro or after being placed in an eye, or, more specifically, after being placed in the anterior chamber the eye.

The one or more biodegradable polymers used to form the matrix (polymer material of the implant) are desirably subject to enzymatic or hydrolytic instability. Additional preferred characteristics of the polymer(s) include biocompatibility, compatibility with the therapeutic component, ease of use of the polymer in making the implant of the present invention, a half-life in the physiological environment of at least about 6 hours, preferably greater than about one day, and water insolubility.

A biodegradable polymer material preferably degrades in vivo in a manner that provides for release of a therapeutically effective amount of the therapeutic agent for a period that is significantly greater than the in vivo life of the agent when administered in an eye drop formulation. As previously discussed, a polymer material may be a single polymer or copolymer, or, in some instances, a combination or blend of biodegradable polymers and/or copolymers.

In addition to the biodegradable polymer(s) and Compound having Formula I, II, III, or IV, an intraocular implant according to this invention may comprise one or more excipients to improve the stability (e.g., shelf life) of the therapeutic agent in the final implant, the ease of manufacture and handling of the implant, and/or the release characteristics of the implant. Compound 1, for example, is susceptible to oxidative degradation under various manufacturing, formulation, and storage conditions. The main degradation product is believed to be the C-15 ketone.

Examples of excipients for any of these purposes may include preservatives, antioxidants, buffering agents, chelating agents, electrolytes, or other excipients. In general, the excipient, when present, may constitute 0.001 to 10% or up to 15% by weight of the implant, and may be selected from any of those named below.

Useful water soluble preservatives may include sodium bisulfite, sodium bisulfate, sodium thiosulfate, benzalkonium chloride, chlorobutanol, thimerosal, phenylmercuric acetate, phenylmercuric nitrate, methylparaben, benzyl alcohol, polyvinyl alcohol and phenylethyl alcohol.

Suitable water soluble buffering agents are alkali or alkaline earth carbonates, phosphates, bicarbonates, citrates, borates, acetates, succinates, and the like, such as sodium phosphate, citrate, borate, acetate bicarbonate, and carbonate. These agents may be present in amounts sufficient to maintain a pH of the hydrated implant of between 2 to 9 and preferably 4 to 8. As such the buffering agent may be as much as 5% on a weight to weight basis of the total composition.

Suitable electrolytes may include sodium chloride, potassium chloride, and the like, including $MgCl_2$. Zinc salts may also be of interest.

Examples of antioxidants include ascorbate, ascorbic acid, L-ascorbic acid, melatonin, butylated hydroxyanisole, thiols, polyphenols, tocopherols such as alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetylcysteine, carnosine, gamma-glutamylcysteine, quercetin, lactoferrin, dihydrolipoic acid, citrate, *Ginkgo Biloba* extract, tea catechins, bilberry extract, vitamin E or an ester of vitamin E, retinyl palmitate, and derivatives thereof.

Useful chelating agents may be selected from, for example, ethylenediaminetetraacetic acid (EDTA), ethylenediamine, porphine, and vitamin B-12.

Other excipients may include alcohols such as, for example, hexadecanol (also referred to as cetyl alcohol and hexadecan-1-ol, and sometimes denoted as C16-OH). In some embodiments, the implant may comprise a straight chain or branched alcohol that is greater than 10 carbons in length.

In one embodiment an implant may further include polyethylene glycol such as for example polyethylene glycol 3350 (PEG 3350). In other embodiments the implant does not contain PEG 3350.

An implant may include a combination of two or more of the above-named excipients.

Oxygen may be an important element in the degradation pathway of a therapeutic agent such as Compound 1. Other or additional means for extending the shelf life and preserving the potency of the implant once manufactured can comprise the step of storing the implant in an oxygen-depleted or oxygen-poor atmosphere such as in a sealed pouch (e.g., an aluminum pouch) comprising an oxygen absorber pack. Additional steps may include filling the pouch with nitrogen or argon gas before sealing the pouch to further remove oxygen from the pouch.

One embodiment is an intraocular implant according to this disclosure comprising an antioxidant that retains at least 90% or greater than 95% or at least 98% of its initial potency (or that loses no more than 5% or no more than 2% of its initial potency) after storage of the extruded implant for one month or for three months at 25° C. in a sealed pouch comprising an oxygen absorber. The initial potency may be based on the actual or theoretical amount of the active agent (e.g., Compound 1) on a weight to weight basis (w/w) present in the implant immediately after implant manufacture. In some embodiments, the implant may further be contained in a needle-tipped ocular implant delivery device in the pouch and the pouch may further contain a desiccant.

The amount of biodegradable polymer material, and therefore the ratio and/or amount of the particular biodegradable polymer(s) used in an implant may vary depending on the Compound used and the release characteristics desired. A linear or constant, or nearly constant rate of release over a sustained period may be useful for the steady, long term (>1 month, e.g., 3-6 months) reduction of intraocular pressure. In general, the biodegradable polymer material of an implant of this invention may constitute from 1% to 99% of the implant by weight (% w/w). In some embodiments the biodegradable polymer material represents 80% to 99% of the implant by weight (% w/w). In some embodiments, the biodegradable polymer material represents about 92% to about 99% of the implant by weight.

In one embodiment the biodegradable polymer material comprises or consists of first, second, and third biodegradable polymers. The first and second polymers may be poly(D,L-lactide) polymers that differ one from the other by their end group (ester or acid) and/or their inherent viscosity (as determined for a 0.1% solution in chloroform at 25° C.); and the third polymer may be a poly(D,L-lactide-co-glycolide). The implant may optionally further comprise hexadecanol.

In one embodiment, the first polymer is a poly(D,L-lactide) having an ester end group and an inherent viscosity of 0.25-0.35 dl/g (as measured for a 0.1% w/v solution in chloroform at 25° C.) (e.g., R203S); the second polymer is a poly(D,L-lactide) having an acid end group (i.e, a carboxyl end group) and an inherent viscosity of 0.25-0.35 dl/g (as measured for a 0.1% w/v solution in chloroform at 25° C.) (e.g, R203H); and the third polymer is a poly(D,L-lactide-co-glycolide) having an ester end group, an inherent viscosity of 0.16-0.24 dl/g (as measured for a 0.1% w/v solution in chloroform at 25° C.), and a D,L-lactide:glycolide ratio of about 75:25 (e.g., RG752S).

In some embodiments, the first, second, and third biodegradable polymers are independently selected from the group consisting of:

R202H, which is a poly(D,L-lactide) having an acid end group and an inherent viscosity of 0.16-0.24 dl/g, as measured for a 0.1% solution in chloroform at 25° C.;

R203H, which is a poly(D,L-lactide) having an acid end group and an inherent viscosity of 0.25-0.35 dl/g, as measured for a 0.1% solution in chloroform at 25° C.;

R202S, which is a poly(D,L-lactide) having an ester end group and an inherent viscosity of 0.16-0.24 dl/g, as measured for a 0.1% solution in chloroform at 25° C.;

R203S, which is a poly(D,L-lactide) having an ester end group and an inherent viscosity of 0.25-0.35 dl/g, as measured for a 0.1% solution in chloroform at 25° C.; and RG752S, which is a poly(D,L-lactide-co-glycolide) having an ester end group and an inherent viscosity of 0.16-0.24 dl/g (as measured for a 0.1% solution in chloroform at 25° C.), and a D,L-lactide:glycolide molar ratio of about 75:25.

In one embodiment, the first polymer is a poly(D,L-lactide) having an ester end group and an inherent viscosity of 0.25-0.35 dl/g, the second polymer is a poly(D,L-lactide) having an acid end group and an inherent viscosity of 0.16-0.24 dl/g, and the third polymer is a poly(D,L-lactide-co-glycolide) having an ester end group and an inherent viscosity of 0.16-0.24 dl/g and a D,L-lactide:glycolide ratio of about 75:25, where the inherent viscosity of each polymer or copolymer is measured for a 0.1% solution of the polymer or copolymer in chloroform at 25° C.

In one specific embodiment, the first polymer is R203S, the second polymer is R202H, and the third polymer is RG752S, and the implant further comprises the excipient hexadecan-1-ol. In specific forms, the implant comprises from 0.001% to 10% by weight of the hexadecan-1-ol.

In another embodiment, the biodegradable polymer material comprises or consists of first and second biodegradable polymers, wherein the first polymer is a poly(D,L-lactide) having an ester end group and an inherent viscosity of 0.25-0.35 dl/g (as measured for a 0.1% w/v solution in chloroform at 25° C.) (e.g., R203S) and the second polymer is a poly(D,L-lactide) having an acid end group (i.e, carboxyl) and an inherent viscosity of 0.25-0.35 dl/g (as measured for a 0.1% w/v solution in chloroform at 25° C.) (e.g, R203H).

In another embodiment, the biodegradable polymer material comprises or consists of a poly(D,L-lactide) having an acid end group (i.e, a carboxyl end group) and an inherent viscosity of 0.16-0.24 dl/g (as measured for a 0.1% w/v solution in chloroform at 25° C.) (e.g, R202H).

In another embodiment, the biodegradable polymer material comprises or consists of a poly(D,L-lactide) having an acid end group (i.e, carboxyl end group) and an inherent viscosity of 0.25-0.35 dl/g (as measured for a 0.1% w/v solution in chloroform at 25° C.) (e.g, R203H).

One embodiment is an extruded biodegradable intracameral implant comprising Compound 1, hexadecan-1-ol (hexadecanol), and a biodegradable polymer material, wherein the biodegradable polymer material comprises or consists of first, second and third polymers, wherein the first polymer is R203S, the second polymer is R202H, and the third polymer is RG752S. The implant may further comprise an antioxidant. Non-limiting examples include Implants 3, 10, and 11, the formulations for which are set forth below in Table 2.

One embodiment is a biodegradable intraocular implant comprising a biodegradable polymer material, hexadecan-1-ol, and about 8% by weight of a compound having the formula

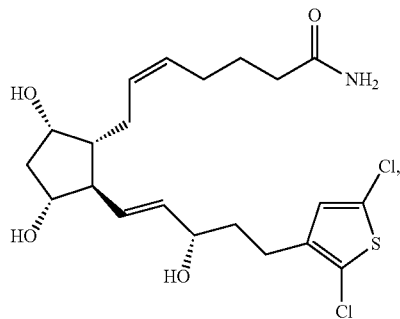 [SMILES: NC(=O)CCC/C=C\C[C@@H]1[C@@H](/C=C/[C@@H](O)CCc2cc(Cl)sc2Cl)[C@H](O)C[C@@H]1O]

wherein the compound and the hexadecane-1-ol are associated with the biodegradable polymer material, and wherein the biodegradable polymer material comprises i) a poly(D,L-lactide) having an ester end group and an inherent viscosity of about 0.25-0.35 dl/g, ii) a poly(D,L-lactide) having an acid end group and an inherent viscosity of about 0.16-0.24 dl/g, and iii) a poly(D,L-lactide-co-glycolide) having an ester end group, an inherent viscosity of about 0.16-0.24 dl/g, and a D,L-lactide:glycolide ratio of about 75:25, wherein the inherent viscosity of each poly(D,L-lactide) and poly(D,L-lactide-co-glycolide) as given above is measured for a 0.1% solution of the polymer in chloroform at 25° C. In some embodiments the implant is an extruded implant. In one embodiment the implant further comprises an antioxidant, a chelating agent, or both an antioxidant and a chelating agent. In specific forms the antioxidant is butylated hydroxyanisole or ascorbic acid and the chelating agent is EDTA. The intraocular implant may be sized for placement in the anterior chamber of the eye.

One specific embodiment is an intraocular implant comprising about 8% by weight of a compound having the formula

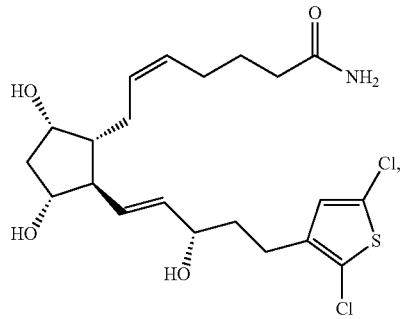 [SMILES: NC(=O)CCC/C=C\C[C@@H]1[C@@H](/C=C/[C@@H](O)CCc2cc(Cl)sc2Cl)[C@H](O)C[C@@H]1O]

and
about 5.6% by weight hexadecan-1-ol, about 50.3% by weight R203S, which is a poly(D,L-lactide) having an ester end group and an inherent viscosity of about 0.25-0.35 dl/g, about 22.4% by weight RG752S, which is a poly(D,L-lactide-co-glycolide) having an ester end group and an inherent viscosity of about 0.16-0.24 dl/g and a D,L-lactide:glycolide ratio of about 75:25, about 11.2% by weight R202H, which is a poly(D,L-lactide) having an acid end group and an inherent viscosity of about 0.16-0.24 dl/g, about 2.0% by weight butylated hydroxyanisole, and about 0.5% by weight EDTA, wherein the inherent viscosities of the R203S, R202H, and RG752S polymers correspond to those measured for a 0.1% solution of the polymer in chloroform at 25° C.

Implants according to any of the embodiments listed above may preferably comprise at least about 1% but no more than about 8% of Compound 1 by weight. For example, Compound 1 may be present in the implant in an amount of between 7 and 9% by weight of the implant. An implant may contain 8.0% by weight Compound 1.

Implants comprising a biodegradable polymer material of the type described above may provide for a constant, steady release of Compound 1 for extended periods, such as 3 months, 4-5 months, or for 6 months.

PLA and PLGA polymers from the RESOMER® polymer product line are available from Evonik Industries AG, Germany.

Specific embodiments include but are not limited to an extruded intraocular implant sized for placement in the anterior chamber of the eye and comprising any one of the formulations given for Implant Nos. 1-4, 10, or 11 in Table 2.

Therapeutic Agents

The present invention includes biodegradable intraocular implants made by an extrusion process that may be effective for reducing intraocular pressure in an eye of a patient for at least one month, for 1-3 months, at least 3 months, for 3-6 months, or for 6 months or more. Generally, the implant comprises or consists of a biodegradable polymer material and a therapeutic agent associated with the biodegradable polymer material. The therapeutic agent may comprise a compound having Formula I, II, III, or IV. In preferred embodiments, the therapeutic agent comprises Compound 1 and the intraocular implant is suitable for placement in the anterior chamber of the eye. The intraocular implant may release from about 10 to about 50 ng of the therapeutic agent per day for at least one month in vitro.

Examples of Compounds having Formula IV, wherein $R^1$ is $-NH_2$ or $-OH$, include Compounds 1 and 2, shown above. Compounds 1 and 2 are of course also embraced by Formula III. Methods for making Compounds 1 and 2 are described in U.S. Pat. No. 5,834,498.

In general, the therapeutic agent of the implant may constitute about 1% to about 90% of the total weight of the implant. In some embodiments the therapeutic agent may represent from 1% to 20% of the total weight of the implant. Preferably, the amount of Compound 1 in an implant on weight to weight basis (w/w) does not exceed 8% of the total weight of the implant. Accordingly, in implants comprising Compound 1, Compound 1 preferably comprises from 1% to 8% of the implant by weight, and in particular forms constitutes 8% of the implant by weight. Restricting the weight percentage of Compound in an implant to these prescribed levels may help avoid undesirably rapid or burst-like release of the drug upon placement of the implant in a liquid environment such as the eye.

A USP approved method for dissolution or release test (USP 23; NF 18 (1995) pp. 1790-1798) can be used to measure the rate of release of a therapeutically active agent such as Compound 1 from an implant. For example, using the infinite sink method, a weighed sample of an implant is added to a measured volume of a solution (release medium) containing 0.9% NaCl (aq) or phosphate buffered saline, where the solution volume will be such that the therapeutically active agent concentration after release is less than 20%, and preferably less than 5%, of saturation. The mixture is maintained at 37° C. and stirred or shaken slowly to ensure diffusion of therapeutically active agent from the implant. The appearance of the therapeutically active agent in the solution or release medium as a function of time may be followed by various methods known in the art, such as spectrophotometry, HPLC, mass spectroscopy, etc.

As described above, an implant according to this invention may comprise a Compound having Formula I, II, III, or IV in the form of a pharmaceutically acceptable salt. The term "pharmaceutically acceptable salts" refers to salts or complexes that retain the desired biological activity of the compound and exhibit minimal or no undesired toxicological effects to the patient or cell system to which they are administered.

The base addition salt form of a compound that occurs in its free form as an acid may be obtained by treating the acid with an appropriate base such as an inorganic base, for example, sodium hydroxide, magnesium hydroxide, potassium hydroxide, calcium hydroxide, ammonia and the like; or an organic base such as for example, L-arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345). Salts formed with zinc are also of potential interest.

The acid addition salt form of a compound that occurs in its free form as a base may be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, or formic acid and the like (Handbook of Pharmaceutical Salts, P. Heinrich Stahl & Camille G. Wermuth (Eds), Verlag Helvetica Chimica Acta-Zürich, 2002, 329-345).

In an implant according to the present disclosure, a Compound having any of Formulas I-IV, such as Compound 1 or Compound 2, may be dispersed or distributed in, and/or covering, and/or surrounded by a biodegradable polymer material. When the implant contacts physiological fluid, such as ocular fluid (e.g. aqueous humor), in vivo, the physiological fluid may contact the portion of the Compound that is on the surface of the implant, but may not have contact with the portion of the Compound that is dispersed inside the polymer material. Once implanted, the biodegradable polymer may begin to be hydrated. Hydration of an implant may improve diffusion and release of the Compound. Additionally, the implant may begin to degrade or erode over time. Degradation may increase hydration, increase the mobility of the polymer chains, and create pores for faster diffusion. Thus, implants may be configured so that the Compound is released from the polymer material as the polymer material is hydrated and/or degrades in vivo. Since hydration decomposition and/or degradation of the implant may take a substantial amount of time—and may be significantly longer than the normal decay period of the Compound when administered by a normal eye drop formulation—an implant may provide sustained release. Sustained release may continue for as long as at least some of the biodegradable polymer material containing at least a portion of the Compound having one of Formulas I-IV remains intact.

The rate at which the Compound having Formula I, II, III, or IV is released from an implant and the duration for which an implant releases the Compound may depend upon a variety of factors including, but not limited to, implant size and shape, particle size of the Compound, the solubility of the Compound, the ratio of the Compound to polymer material, the polymer(s) used (including monomer ratios in the polymer used, polymer end groups, and polymer molecular weight), polymer crystallinity, the method of manufacture, the surface area exposed, polymer material erosion rate, and the biological environment the implants reside in post dosing, etc.

Methods of Manufacture

Various techniques may be employed to make the intraocular implants described herein. Useful techniques may include extrusion methods (for example, hot melt extrusion) to produce rod-shaped implants (or fibers), compression methods to produce tablets, wafers, or pellets, and solvent casting methods to produce biodegradable sheets, films, and dry powders. Emulsion methods to produce a plurality of microspheres may also be of use in preparing a biodegradable intraocular drug delivery system for the sustained release of a Compound having any of Formulas I-IV into an eye in a patient. Accordingly, one embodiment provides for a pharmaceutical composition suitable for placement in an ocular region of an eye and comprising a plurality of biodegradable microspheres encapsulating Compound 1.

An extruded implant can be made by a single or double extrusion method, and may be made with a piston or twin screw extruder, for example. Choice of technique, and manipulation of technique parameters employed to produce the implants can influence the release rates of the drug. Extrusion methods may allow for large-scale manufacture of implants and result in implants with a progressively more homogenous dispersion of the drug within a continuous polymer matrix, as the production temperature is increased. Extrusion methods may use temperatures of from about 60° C. to about 150° C., or from about 70° C. to about 100° C., or lower as necessary.

In one embodiment, an intraocular implant according to the present invention is produced by an extrusion process. Polymers and excipients, if any, are generally blended with the therapeutic agent and then co-extruded at a selected temperature to form a filament comprising a biodegradable polymer matrix (or material) and the therapeutic agent dispersed within and/or distributed throughout the matrix (or material). If desired the filament may be pulverized and re-extruded to form a double extruded implant.

In one variation of producing implants by an extrusion process, the therapeutic agent, biodegradable polymer(s), and, optionally, one or more excipients are first mixed at room temperature (blended in a container) and then heated to a temperature range of 60° C. to 150° C., for a time period of between 1 and 60 minutes, such as 1 to 30 minutes, 5 minutes to 15 minutes, or 10 minutes. The mixture is then extruded through a nozzle at a temperature of 60° C. to 130° C., or at 75° C. The extruded filament is then cut to desired lengths to produce intraocular implants having a specific weight. The orifice of the nozzle through which the mixture is extruded will generally have a diameter appropriate to the desired diameter of the implant, but if necessary the extruded filament can be pulled from the nozzle to further reduce the diameter of the implant. The extruded implant may be generally cylindrical or non-cylindrical, having a length and diameter (or other dimension as appropriate to non-cylindrical fibers) suitable for placement in an ocular region of the eye such as the anterior chamber or vitreous body.

One possible method for producing an intraocular implant of the present disclosure uses a combination of solvent casting and hot melt extrusion. See, for example, US 2010/0278897. In this method, a dry powder or film is first prepared by dissolving all materials (active agent, polymer(s), and excipients, if any) in an appropriate solvent, such as ethyl acetate, to form a solution. The solution is then cast into a suitable container (e.g., a TEFLON® dish), and then dried in a vacuum oven overnight to form a dry film. The film is then ground into particles, which are collected and extruded by hot melt extrusion (using, for example, a piston extruder) to prepare a filament containing the active agent and one or more biodegradable polymers. The filament may be cut to a length and thereby weight suitable for placement in the eye. The extrusion temperature for this process may range from 45° C. to 85° C.

An extruded filament or implant cut from an extruded filament may be terminally sterilized with electron beam (ebeam) radiation. An effective dose of ebeam radiation may be 20-30 kGy, or more specifically 25 kGy.

Accordingly, the present invention encompasses methods for making and using extruded biodegradable implants (which may be generally referred to as extruded rods or fibers) suitable for placement in an eye of a patient to reduce intraocular pressure, including elevated intraocular pressure in the eye.

Modes and Sites of Administration

To provide for the intended therapeutic effect (e.g., long term reduction of intraocular pressure) in a patient, including one suffering from glaucoma, an implant according to the present invention is preferably placed in the anterior chamber of the eye. The anterior chamber refers to the space inside the eye between the iris and the innermost corneal surface (endothelium). In some patients, however, it may be necessary to place the implant in the vitreous body of the eye. The posterior chamber refers to the space inside the eye between the back of the iris and the front face of the vitreous. The posterior chamber includes the space between the lens and the ciliary process, which produces the aqueous humor that nourishes the cornea, iris, and lens and maintains intraocular pressure. Referring to FIG. 1, these and other ocular regions of the eye (100) are shown in cross-section. Particular regions of the eye (100) include the cornea (102) and iris (104), which surround the anterior chamber (106). Behind the iris (104) is the posterior chamber (108) and lens (110). Within the anterior chamber is the anterior chamber angle (112) and trabecular meshwork (114). Also shown are the corneal epithelium (118), sclera (116), vitreous (119), ciliary zonules (120), and ciliary process (121). The posterior segment of the eye is the rear two-thirds of the eyeball (behind the lens), and includes the vitreous, the retina, and the optic nerve.

To reduce intraocular pressure and treat glaucoma in a patient, an implant described herein may be implanted into the anterior chamber (or other ocular region) of an eye of a mammal as monotherapy to deliver a therapeutic agent (such as Compound 1) into the anterior chamber of the eye without the need for eye drops. Alternatively, the implant may be used with eyedrops as an adjunctive therapy. In some embodiments, inserting an implant described herein into the anterior chamber of an eye may reduce intraocular pressure in the eye by at least about 20% or 30% or more as compared to the baseline IOP for 1 month, 2 months, 3 months, 4 months, or 6 months or more after placement in the eye of a patient. The patient may be a human or non-human mammal suffering from elevated intraocular pressure or glaucoma and therefore in need of treatment. In some embodiments, the implant may release Compound 1 according to linear or pseudo zero order kinetics for at least one month after placement of the implant in an eye.

Biodegradable implants may be inserted into an eye by a variety of methods, including placement by forceps, by trocar, or by a hand-held needle-equipped (or needle-tipped) delivery device (applicator). Some hand held applicators may be used to insert one or more biodegradable implants into the eye. Hand held applicators may comprise an 18-30 GA (gauge) stainless steel needle, a lever, an actuator, and a plunger or push rod to facilitate ejection of the implant. An implant may be inserted by a scleral, limbal, or corneal route to access the anterior chamber. Alternately, an implant may be inserted into the vitreous using an appropriate applicator with a needle or cannula of length suitable for accessing the target site and delivery of the implant. Some methods for inserting an implant include accessing the target area within the ocular region with a needle, trocar or implantation device. Once within the target area, e.g., the anterior chamber or the vitreous, a lever on a hand held device can be depressed to cause an actuator to drive a plunger or push rod forward. As the plunger moves forward, it can push the device or implant into the target area (such as the vitreous or the anterior chamber). One example of an ocular implant delivery device is disclosed in U.S. Patent Application Publication 2004/0054374.

Accordingly, methods for treating glaucoma and reducing intraocular pressure in an eye of a patient as discussed herein may comprise administering an biodegradable intraocular implant of the type presently disclosed to the eye by injection into the anterior chamber (intracameral injection) or vitreous body of the eye (intravitreal injection). A syringe apparatus including an appropriately sized needle (for example, a 22, 25, 27, 28, or 30 gauge needle) may be useful for injecting one or more implants into these regions in the eye. Accordingly, the width or diameter of the implant may be selected so as to allow the implant to be received in and translated through the lumen of the needle gauge selected.

Prior to use in a subject, an implant may be sterilized with a suitable dose of beta-radiation. Preferably, the sterilization method does not substantially reduce the therapeutic activity of the therapeutic agent in the implant or preserves at least 50 or 80% or more of the initial activity.

Accordingly, the present invention includes, but is not limited to, the following embodiments (1-16):

1. A biodegradable intraocular implant comprising a biodegradable polymer material and a therapeutic agent associated with the biodegradable polymer material, wherein the therapeutic agent comprises a compound having the formula (I)

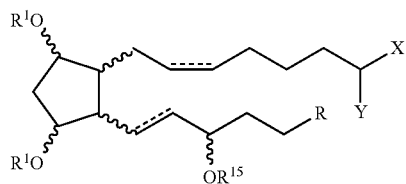

or a pharmaceutically acceptable salt or ester prodrug thereof, wherein the wavy segments represent an α or β bond, dashed lines represent a double bond or a single bond, R is a substituted heteroaryl radical, wherein each $R^1$ is independently selected from the group consisting of hydrogen and a lower alkyl radical having up to six carbon atoms, X is $-OR^1$, $-N(R^1)_2$, or $-N(R^5)SO_2R^6$, wherein $R^5$ represents hydrogen or $CH_2OR^6$, $R^6$ represents hydrogen, a lower alkyl radical having up to six carbon atoms, a halogen substituted derivative of said lower alkyl radical, or a fluoro substituted derivative of said lower alkyl radical, and $R^{15}$ is hydrogen or a lower alkyl radical having up to six carbon atoms; and Y is =O or represents 2 hydrogen radicals, wherein the substituent(s) on the substituted heteroaryl radical in Formula I is/are selected from the group consisting of $C_1$ to $C_6$ alkyls, halogens, trifluoromethyl, $COR^1$, $COCF_3$, $SO_2N(R^1)_2$, $NO_2$, and CN.

2. A biodegradable intraocular implant comprising a biodegradable polymer material and a therapeutic agent associated with the biodegradable polymer material, wherein the therapeutic agent comprises a compound having the formula (III)

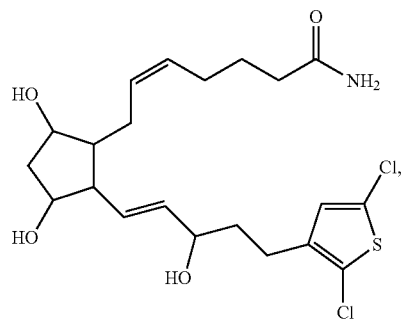 [SMILES: NC(=O)CCC/C=C\CC1C(O)CC(O)C1/C=C/C(O)CCc1cc(Cl)sc1Cl]

or a pharmaceutically acceptable salt or ester prodrug thereof, wherein X is $-OH$ or $-N(R^1)_2$, and wherein $R^1$ is independently selected from the group consisting of hydrogen and $C_1$-$C_6$ alkyl, and wherein the implant is effective for reducing intraocular pressure (IOP) in a mammalian eye.

3. An intraocular implant according to embodiment 2, wherein the therapeutic agent comprises a compound having the formula (IV)

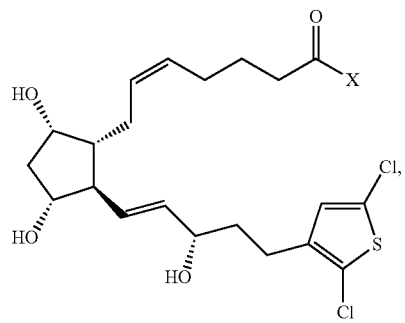

or a pharmaceutically acceptable salt or ester prodrug thereof, wherein X is $-OH$ or $-N(R^1)_2$, wherein $R^1$ is independently selected from the group consisting of hydrogen and a $C_1$-$C_6$ alkyl.

4. An intraocular implant according to embodiment 3, wherein the therapeutic agent comprises a compound having the formula (Compound 1)

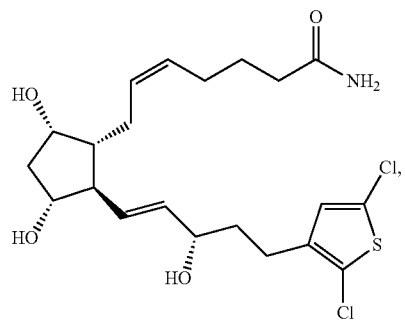 [SMILES: NC(=O)CCC/C=C\C[C@@H]1[C@@H](/C=C/[C@@H](O)CCc2cc(Cl)sc2Cl)[C@H](O)C[C@@H]1O]

wherein the implant is effective for reducing IOP in a mammalian eye for 5 months or more after placement in the eye.

5. An intraocular implant according to any of embodiments 1-4, wherein the implant is sized for placement in the anterior chamber of the eye.

6. An intraocular implant according to any of embodiments 1-5, wherein the biodegradable polymer material comprises a poly(D,L-lactide), poly(D,L-lactide-co-gly-colide), or a combination thereof.

7. An intraocular implant according to embodiment 4, wherein the implant is effective for reducing IOP in a mammalian eye by 20-30% for 5 months or more relative to the IOP in the eye before receiving the implant.

8. The implant of embodiment 4, wherein the therapeutic agent represents at least about 1% but no more than about 8% of the implant by weight.

9. An implant according to any embodiments 1-8, wherein the implant is produced by an extrusion process, and wherein the implant is about 0.5 to about 2 mm in length, about 100 to about 500 μm in diameter, and about 10 to about 200 μg in total weight.

10. A method for reducing intraocular pressure in a patient, comprising administering a therapeutically effective amount of a therapeutic agent to the anterior chamber of an eye in the patient, thereby reducing intraocular pressure in the eye, wherein the therapeutic agent has the formula

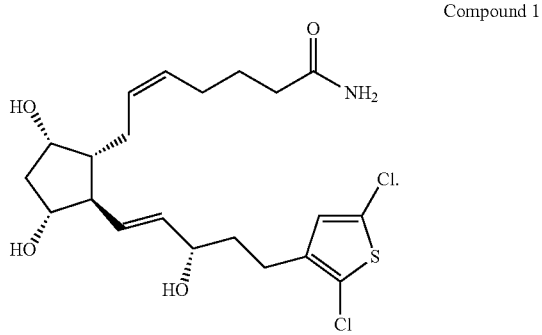

Compound 1

11. A method for reducing intraocular pressure in a patient, comprising placing an intraocular implant according to any of embodiments 1-9 in an eye of the patient, thereby reducing intraocular pressure in the eye for 5 months or more.

12. The method of embodiment 10 or 11, wherein the patient is suffering from, diagnosed with, or at risk of developing elevated intraocular pressure or glaucoma.

13. A method according to any of embodiments 11-12, wherein the intraocular implant is placed in the anterior chamber of the eye in the patient.

14. A method according to any of embodiments 11-13, wherein the intraocular implant reduces the intraocular pressure in the eye by at least about 30%, relative to the intraocular pressure in the eye before receiving the implant, for 3-5 months or more following placement in the eye.

15. A method for making a biodegradable intraocular implant effective for reducing intraocular pressure in a patient, the implant comprising or consisting of a biodegradable polymer material and a therapeutic agent associated with the biodegradable polymer material, wherein the therapeutic agent has the formula (Compound 1)

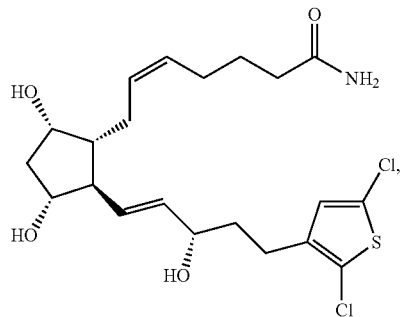

Compound 1 and wherein the method comprises in order I) obtaining Compound 1 in the form of a solid; II) blending said solid form of Compound 1 with a biodegradable polymer or two or more biodegradable polymers to form a mixture, III) extruding the mixture to form a filament, and IV) cutting the filament to lengths suitable for placement in an ocular region of an eye, thereby forming the intraocular implant, wherein obtaining Compound 1 in the form of a solid comprises
a) adding an oil form of Compound 1 to ethyl acetate (EtOAc) at approximately 50° C. to form a mixture;
b) agitating the mixture of step a) at 50° C. to form a clear solution;
c) cooling the clear solution of step b) to approximately 30° C. for 1-3 hours;
d) adding a seed crystal of Compound 1 to the cooled solution of step c);
e) maintaining the seeded solution of step d) at about 30° C. for 1-3 hours;
f) cooling the seeded solution from step e) to a temperature of from about 0-5° C. over the course of about 1-5 hours;
g) agitating the solution from step f) at a temperature of from about 0-5° C. for 1-3 hours to form a suspension;
h) filtering the suspension at a temperature of between about 20° C. and 25° C. to thereby produce a solid form of Compound 1, and wherein the seed crystal of Compound 1 is prepared by the method comprising
i) dissolving an oil form of Compound 1 in EtOAc at a temperature of from about 35-40° C. to form a mixture;
ii) agitating the mixture of step i) at a temperature of from about 35-40° C. to form a clear solution;
iii) cooling the clear solution of step ii) to a temperature of from about 0-5° C. over the course of about 1-5 hours;
iv) agitating the cooled solution from step iii) a temperature of from about 0-5° C. for 1-3 hours to form a white suspension;
v) filtering the white suspension from step iv) at a temperature of between about 20° C. and 25° C. to thereby produce seed crystal of Compound 1.

16. Another embodiment is a method for preparing a crystal form of Compound 1 according to steps i-v, above.

Example 1

Comparison of IOP Lowering Activities of Prostamides In Vivo

Compound 1 falls within a class of compounds known collectively as prostamides (Woodward et al. (2007) *British Journal of Pharmacology* 150:342-352).

A series of prostamides were selected as potential candidates for an intracameral biodegradable drug delivery system (e.g., an implant) and tested for their ability to lower IOP by direct administration to the aqueous humor (therefore, by intracameral administration). Table 1 lists the $EC_{50}$ values (nM) obtained from the feline (cat) iris assay, calculated log P values (cLog P), and IOP reduction values obtained after either topical or intracameral administration for different prostamides. Intracameral drug administration was accomplished by placing an infusion pump in the subcutaneous pocket in the neck of dogs with a cannula running into the anterior chamber of the eye. Test runs were carried out to measure and compare the concentration of the compound in the solution exiting the pump with that initially added to the pump in order to confirm the dosing level. As shown by Table 1, Compound 1 reduces IOP effectively and much more efficiently than bimatoprost when administered intracamerally (directly to the anterior chamber) to a normotensive dog eye.

The molecular structures of Compounds 3-5 are shown below. Disclosure relating to Compounds 3-5, including synthetic methods, may be found in U.S. Pat. Nos. 6,602,900, 6,124,344, 5,834,498, and/or 5,688,819, as the case may be. Reference may also be found in WO 95/18102, WO 96/36599 and WO 99/25358, US 2007/0099984, and U.S. Pat. No. 5,741,810, and Schuster et al. (2000) *Mol. Pharmacol.* 58:1511-1516.

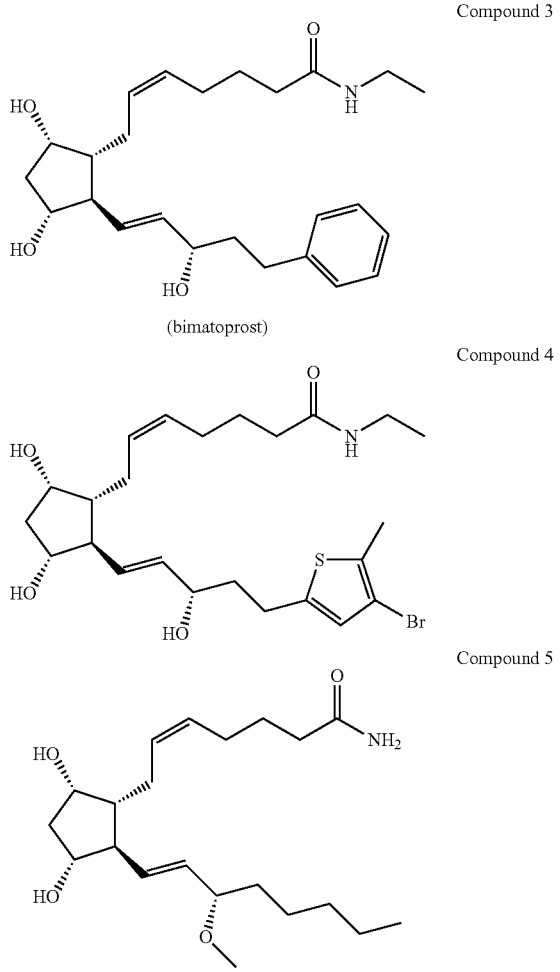

TABLE 1

Prostamide/FP receptor and IOP-lowering activity of select prostamides.

| Compound | cLog P | Cat Iris Sphincter Assay*** $EC_{50}$ (nM) | Topical Administration (dogs)** Concentration % (w/v) | Topical Administration (dogs)** IOP reduction (mm Hg) | Intracameral Administration (dogs)* Dose (ng/day) | Intracameral Administration (dogs)* Max IOP reduction (%) |
|---|---|---|---|---|---|---|
| Compound 3 (Bimatoprost) | 2.0 | 34 | 0.01% | −3.6 | 108 | ~45% |
| Compound 1 | 2.2 | 0.71 | 0.03% | −5 | 15 | ~35% |
| Compound 5 | 1.9 | 20 | 0.01% | −3 to −4 | 100 | ~20% |
| Compound 4 | 2.8 | 25 | 0.03% | −3 | 15 | <10% |

The symbol "~" means approximately
The symbol "<" means less than
cLog P (calculated log P) is a measure of the lipophilicity of the Compound. The partition coefficient (P) for each Compound is determined by calculating the ratio of the equilibrium concentrations of the dissolved unionized Compound in each phase of a two-phase system consisting of n-octanol and water.
*Test compounds were administered directly into the anterior chamber (intracamerally) at doses ranging from 15 ng/day to 108 ng/day using an infusion pump implanted subcutaneously in the animals. Only the right eyes were surgerized and dosed while the left eyes remained untreated to serve as the control. The number of animals treated ranged from 3-5. Infusion of test compounds to the right eyes was maintained for 2-3 weeks while IOP measurements were obtained from both eyes 3 times per week using a TonoVet tonometer. The % IOP lowering was calculated as the observed percent difference in IOP at the time of measurement after initiation of the infusion compared to baseline prior to the start of the infusion. A dose level of 15 ng/day was selected for compounds of interest based on assumption of drug loading in an IC DDS and its size limitation given the intended site of dosing.
**The effects of the compounds on intraocular pressure in dogs when administered topically to the eye was measured. The compounds were prepared at the indicated concentrations in a vehicle comprising 0.1% polysorbate 80 and 10 mM TRIS base. Normotensive dogs were treated by administering 25 μL to the ocular surface of one eye, the contralateral eye received vehicle as a control. Intraocular pressure was measured by applanation pneumotonometry. Dog intraocular pressure was measured immediately before drug administration and at 6 hours thereafter.
***The prostamide/FP receptor activity of each compound was measured as a contraction of the isolated feline (cat) iris sphincter muscle.

Example 2

Biodegradable Intracameral Implants for Sustained Delivery of Compound 1 In Vivo Additional studies were undertaken to identify a biodegradable formulation that could be manufactured in the form of an extruded implant suitable for placement in the anterior chamber of an eye and capable of providing near zero order release of Compound 1 for at least three months, and preferably for at least six months after placement in the anterior chamber of the eye. A further requirement was that the implant should be well tolerated by the eye, producing little if any adverse reactions such as for example pain, redness, or inflammation. With these goals in mind, a series of extruded implants (including, for example, Implants 1-9) were prepared and tested in vitro and in vivo, as described below. The compositions, dimensions, and weights of Implants 1-9 are given in Table 2. The biodegradable polymers used to prepare the implants were selected from among the RESOMER® polymers available from Evonik Industries, AG, and are designated according to their polymer identification number in Table 2.

Manufacture of Implants Using a Twin Screw Extruder

Implants 1-4, 10, and 11 in Table 2 were manufactured by hot melt extrusion using a twin screw extruder (DSM Xplore 5 Micro Extruder) as follows.

Prior to extrusion, a pure solid form of Compound 1 was prepared by dissolving the crude Compound 1 in ethyl acetate (EtOAc) at approximately 50° C. and agitating at that temperature until a clear solution was obtained. This clear solution was then slowly cooled to a temperature of approximately 30° C. over a period of time before seeding it with Compound 1 seed crystal. This solution was held at approximately 30° C. for a period of time before cooling it down to 0-5° C. over a few hours, and continuing to agitate it at that temperature for a period of time. The suspension was then filtered at ambient temperature to afford pure Compound 1.

A seed crystal form of Compound 1 was prepared by dissolving the pure Compound 1 (an oil after chromatography purification) in EtOAc at approximately 35-40° C. and agitating at that temperature until a clear solution was obtained. This clear solution was then slowly cooled to a temperature of approximately 0-5° C. over a few hours, and then agitated at that temperature for a period of time. A white suspension was formed and then filtered at ambient temperature to afford seed crystal of Compound 1.

Before starting the extrusion, the polymer(s), a pure solid form of Compound 1 (prepared as given above), and excipients, if any, were blended to ensure uniformity. To uniformly blend the implant components before extrusion, Compound 1, polymer(s), and excipient (if present) were accurately weighed and transferred into a small stainless steel container with two stainless steel balls. The materials were blended using a Turbula mixer for 20 to 45 minutes. The powder blend was manually mixed again with a spatula after blending. The DSM twin screw extruder was assembled and pre-heated to the desired extrusion temperature (normally, between 60° C. to 100° C.). The blended material was then fed manually into the opening at the top of the barrel between the two turning screws. The melt materials were conveyed down the barrel by the turning screws and extruded from a 500 μm nozzle. The diameter of the extruded filament was controlled by a Beta Lasermike puller that was attached to the equipment. The diameter of filaments was adjusted by changing the puller speed. The final diameter of the filament generally ranged from 0.006 inches to 0.025 inches. Extruded filaments were then cut to 5 to 10 inch lengths and collected into a storage tube. The storage tube was placed in an aluminum foil pouch with a desiccant and oxygen absorber combo pack, heat sealed, and stored in a −20° C. freezer.

Manufacture of Implants Using a Piston Extruder

Implants 5-9 in Table 2 were manufactured using a solvent casting/hot melt extrusion method with a mechanically driven ram micro extruder (piston extruder). The drug substance (Compound 1, in the form of an oil), polymer(s) and excipients, if any, were dissolved together in ethyl acetate to form a single solution. The solution was cast into a TEFLON® dish and dried overnight in a vacuum oven at 35° C. to form a film. The film was ground into particles which were then placed into the heated well of a piston extruder and extruded into 200-250 μm diameter filaments using a piston extruder at a temperature range of 45-85° C. through a 200 μm nozzle and a speed setting number of 0.0025. Smaller implants were manufactured by using a smaller nozzle or pulling at a faster rate. Extruded filaments were cut into 5 inch lengths and collected into a storage tube. The storage tube was placed in an aluminum foil pouch with a desiccant and oxygen absorber combo pack, heat sealed, and stored in a −20° C. freezer.

In Vitro Release Rate Assay

To measure the in vitro release rate and determine the cumulative in vitro release profile of each implant formulation in a liquid environment, three 1.5 mm implants were cut from three randomly selected filaments from each lot of filaments for each formulation. Each implant was placed into a 8 mL glass vial containing 3 mL of 0.01 M phosphate buffered saline (pH 7.4) (release medium). The vials were then placed into a shaking water bath set at 37° C. and 50 rpm. At various time points, the vials were removed from the bath and the entire volume of release medium (3 mL) was removed and analyzed by HPLC for the total amount of released prostamide. Immediately after removing the release medium from the vial, 3 mL of fresh phosphate buffered saline was added to the vial and the vial was put back in the water bath for further incubation until the next sampling time point. A cumulative in vitro release curve (or profile) was constructed from the prostamide content values obtained from the HPLC analysis.

The cumulative amount of compound released is expressed as a percent of the total amount of compound initially present in the implant. To determine the total amount of compound initially present in an implant, approximately 4 mg of each tested filament was weighed and transferred to a 5 mL volumetric flask. Next, 2.5 mL of acetonitrile was added to each flask. The flasks were vortexed and swirled to completely dissolve the filament. Water was then added to the flask to bring the volume to 5 mL. After the flask was mixed well, approximately 1.5 mL of the solution was transferred to a microcentrifuge tube and centrifuged for 10 minutes at 12,000 rpm. A portion of the clear supernatant was transferred to a HPLC vial for analysis of the prostamide (for example, Compound 1) content.

In Vivo Intraocular Pressure (IOP) Lowering Studies

The IOP lowering effect of Implants 1-4 was tested in normotensive dogs. A total of eight normotensive dogs were treated with each implant. In preparation for in vivo IOP lowering studies, each implant (having the dimensions, weight, and composition set forth in Table 2) was loaded into a needle-tipped delivery device (one implant per device). The entire assembly (device and implant) was then sterilized with 20-25 kGy of electron beam radiation. Each dog received one implant in the anterior chamber of the right eye while the left eye were left untreated to serve as the control. IOP measurements were obtained from both eyes before and post dosing at a frequency of 3 times per week for ~5 months post dose. The % IOP lowering was calculated as the observed percent difference in IOP at the time of measurement after dosing compared to baseline. The average % reduction in IOP for the treated and untreated eyes observed for each group of eight dogs are shown in FIGS. 5-8. Comparing in vivo duration of efficacy to the in vitro release profile for Implants 1-4, it was clear that IOP lowering effect in normotensive dogs lasted much longer than what might have been expected based on the results from the in vitro release studies, a surprising yet favorable finding.

Figure 2:
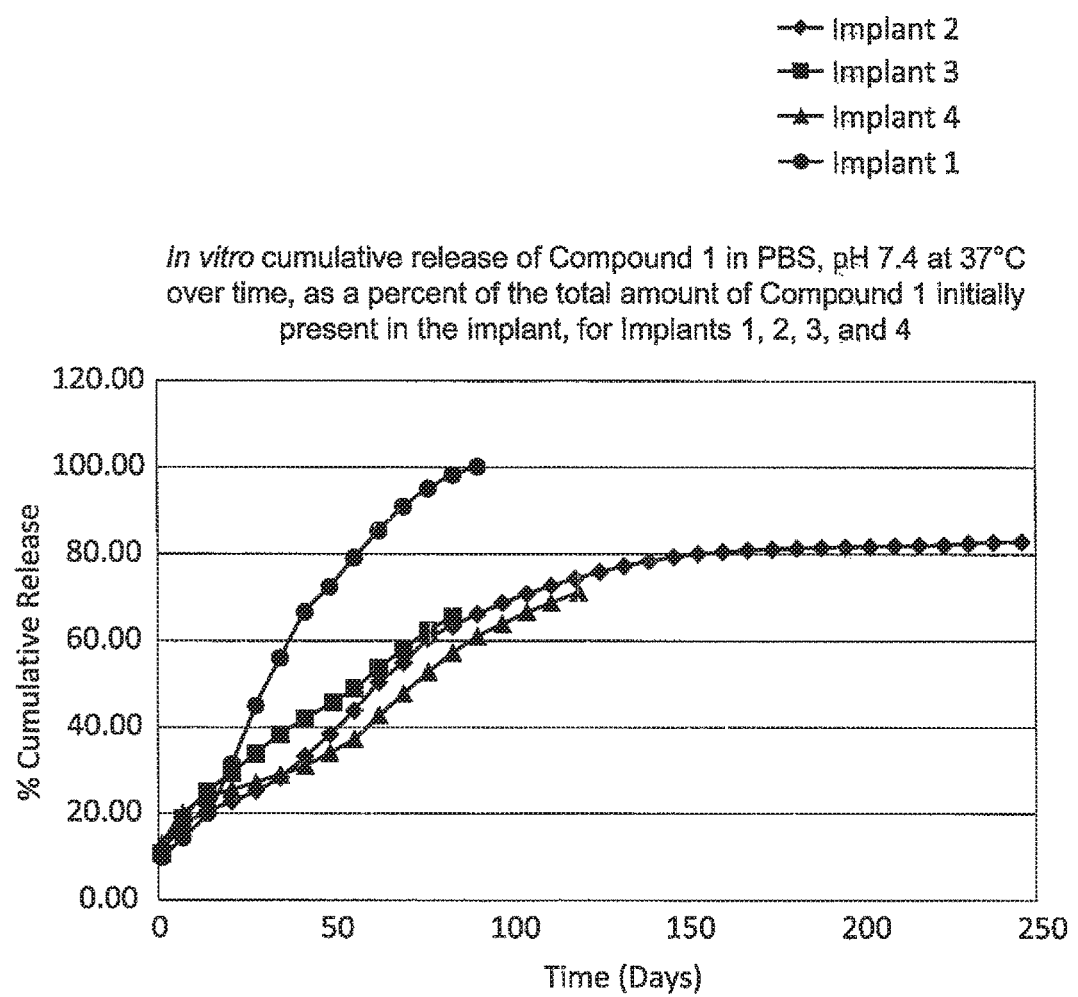
FIG. 2. shows the in vitro cumulative total percent release of Compound 1 into phosphate buffered saline (0.01 M; pH 7.4) at 37° C. over time for four (4) separate implants (Implants 1-4) prepared with a twin screw extruder. The composition of each implant is described in Table 2.
Figure 3:
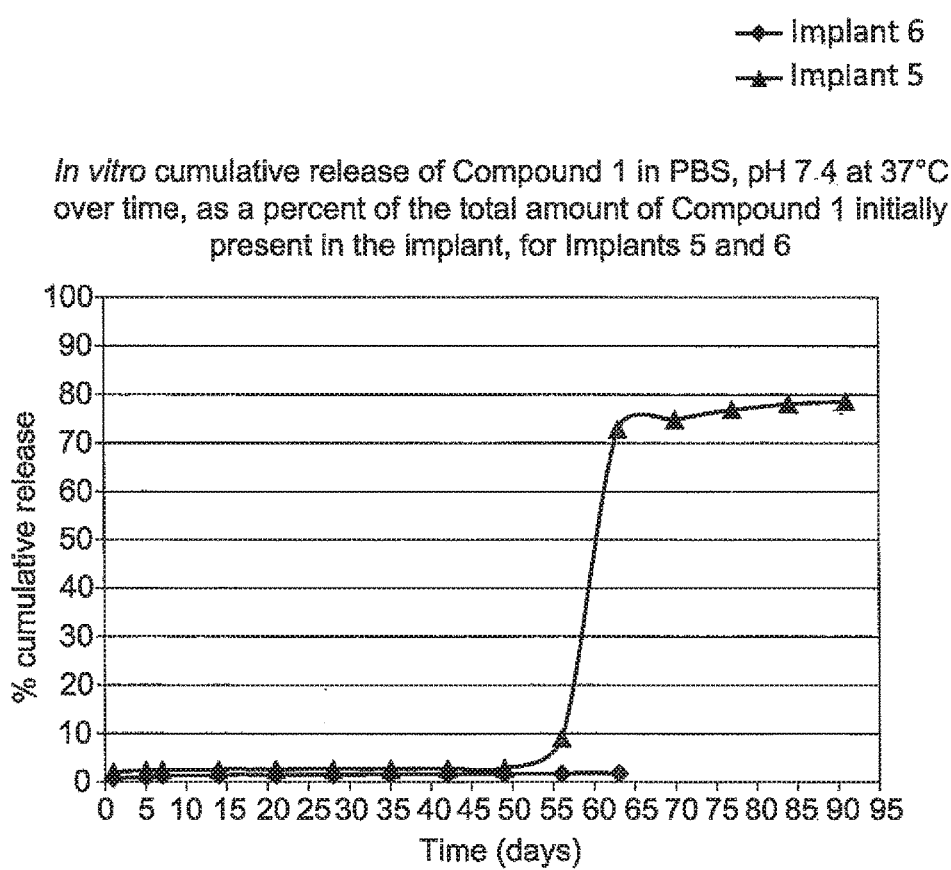
FIG. 3 shows the in vitro cumulative total percent release of Compound 1 into phosphate buffered saline (0.01 M; pH 7.4) at 37° C. over time for Implants 5 and 6, prepared with a piston extruder. The composition of each implant is set forth in Table 2.
Figure 4:
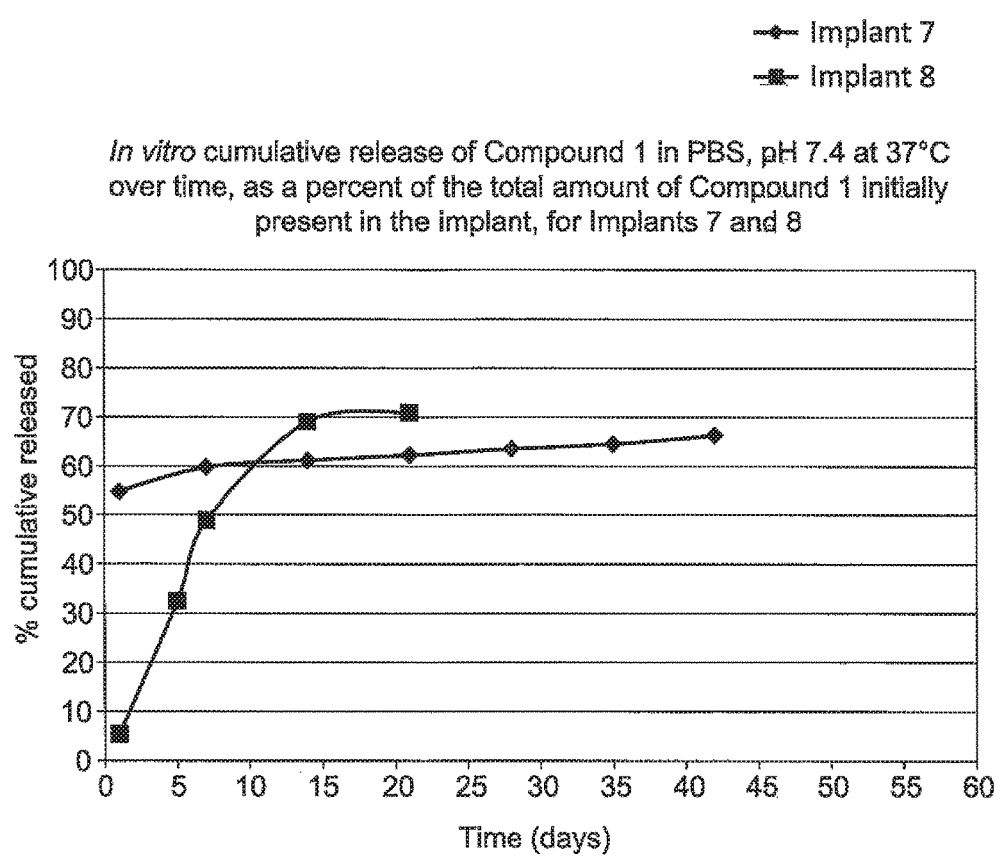
FIG. 4 shows the in vitro cumulative total percent release of Compound 1 into phosphate buffered saline (0.01 M; pH 7.4) at 37° C. over time for Implants 7 and 8, prepared with a piston extruder. The composition of each implant is set forth in Table 2.
Figure 5:
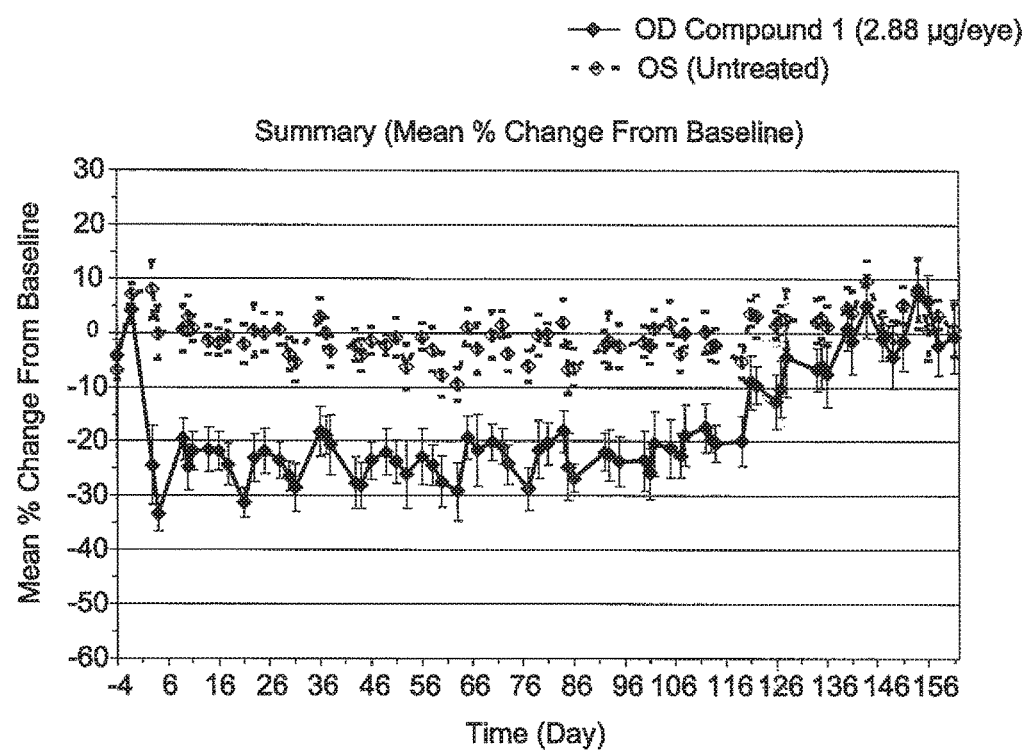
FIG. 5 shows the sustained, intraocular pressure (IOP) lowering effect of Compound 1 in dogs when administered to the eye in the form of an extruded, biodegradable intracameral implant (Implant 1, described in Table 2). A single implant was placed in the anterior chamber of one eye in each dog of the test group. The contralateral eye was left untreated. The test group consisted of 8 dogs (n=8). The mean percent change in IOP relative to the baseline IOP in the treated and untreated eyes for each group was measured at various time points and then plotted as line graph to show the change in IOP over time.
Figure 6:
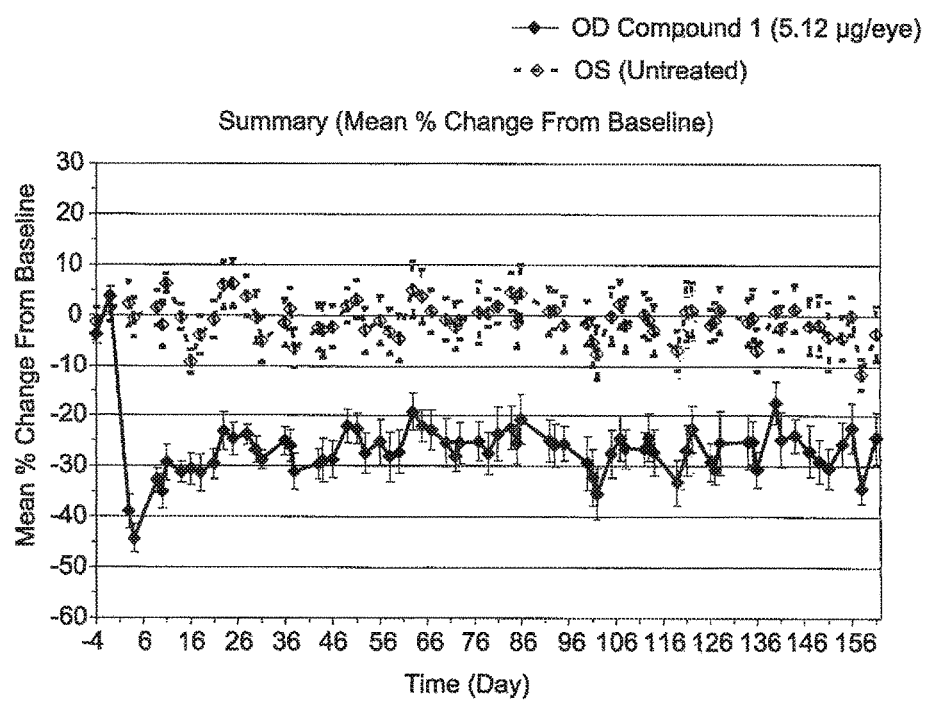
FIG. 6 shows the IOP lowering effect of Implant 2 in dogs (n=8), following placement of a single implant in the anterior chamber of the eye. The in vivo study was carried out as described for FIG. 5 and in Example 2.
Figure 7:
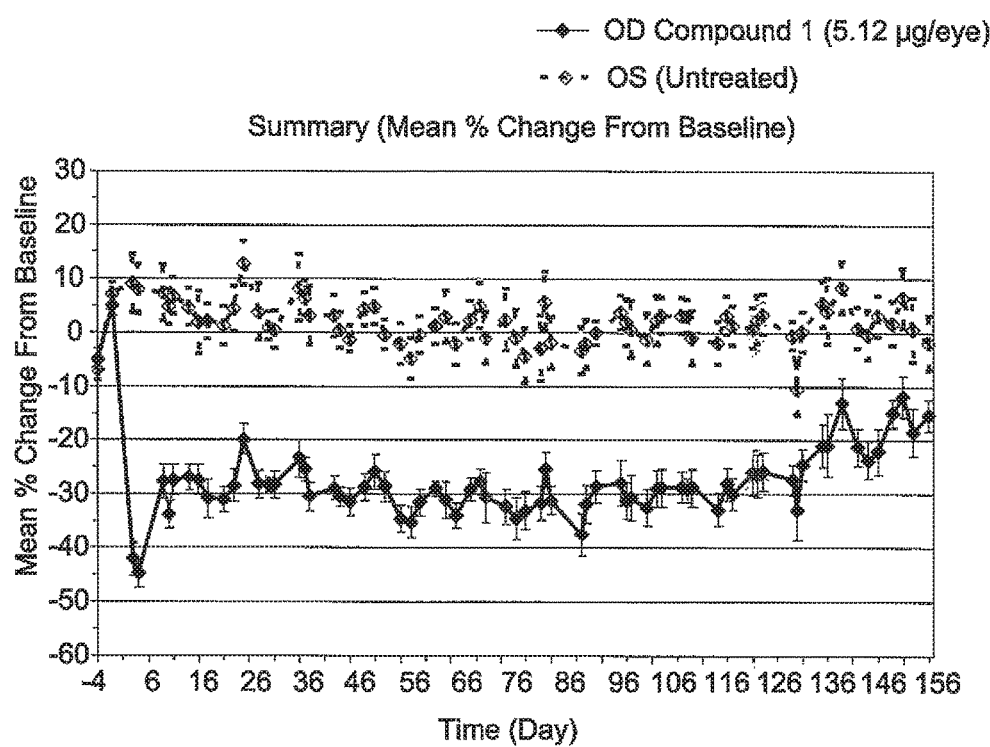
FIG. 7 shows the IOP lowering effect of Implant 3 in dogs (n=8), following placement of a single implant in the anterior chamber of the eye. The in vivo study was carried out as described for FIG. 5 and in Example 2.
Figure 8:
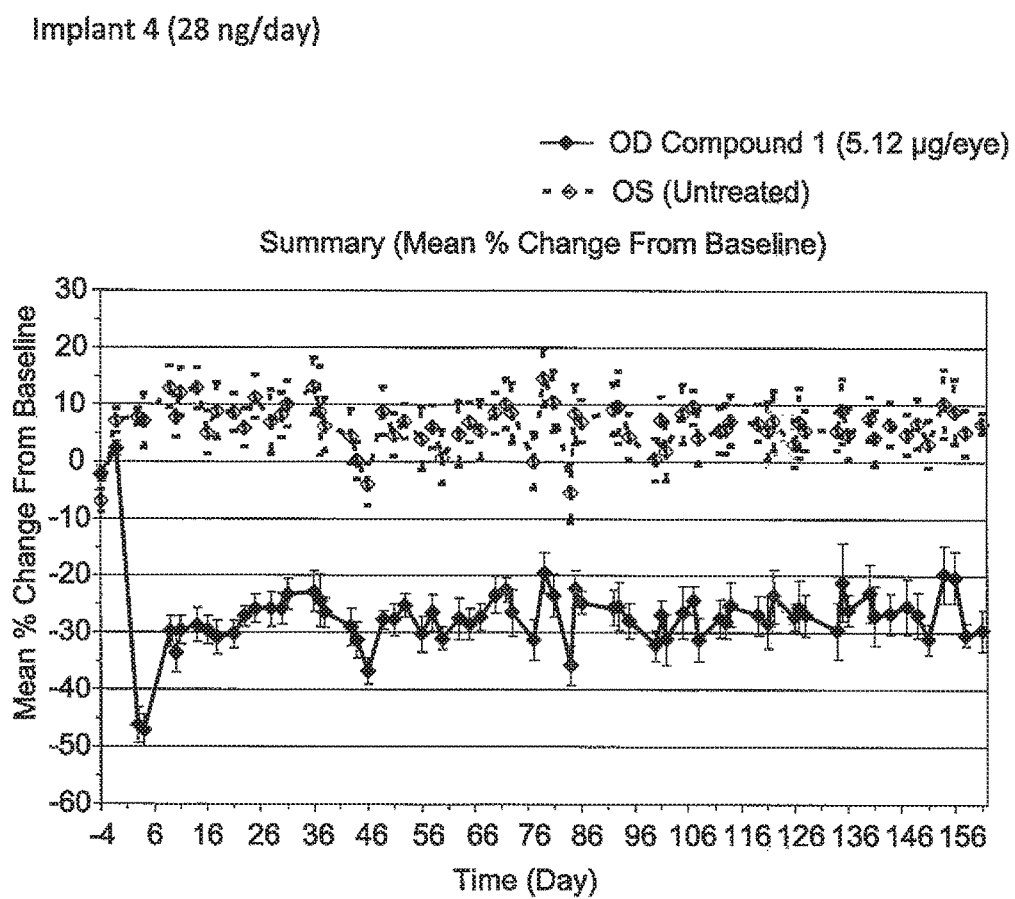
FIG. 8 shows the IOP lowering effect of Implant 4 in dogs (n=8), following placement of a single implant in the anterior chamber of the eye. The in vivo study was carried out as described for FIG. 5 and in Example 2.
Figure 9:
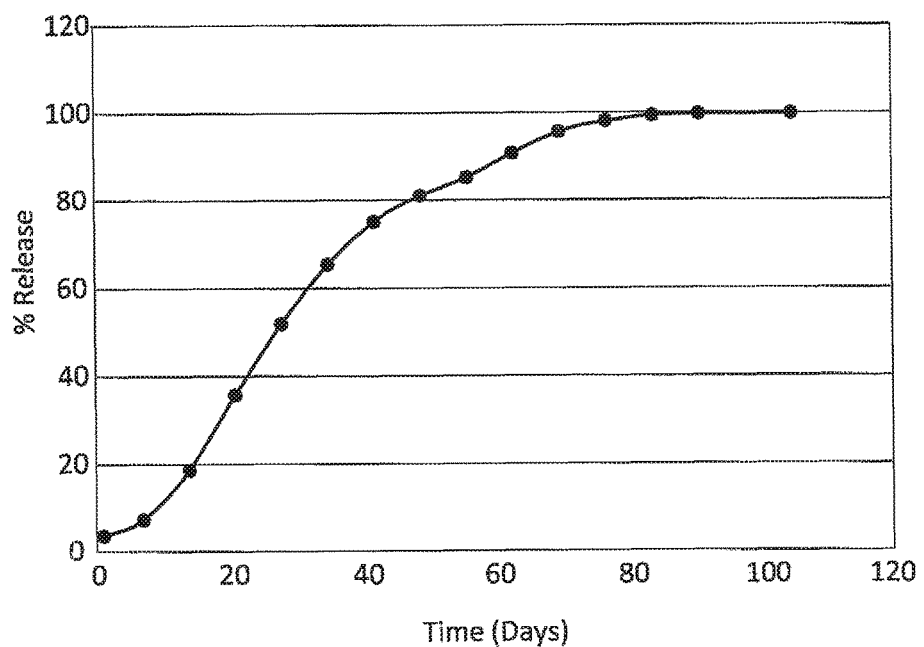
FIG. 9 shows the in vitro cumulative total percent release of Compound 1 into phosphate buffered saline (0.01 M; pH 7.4) at 37° C. over time for Implant 9 prepared with a piston extruder. The composition of Implant 9 is set forth in Table 2.

FIGS. 2-4 and 9 show the cumulative release profiles of Compound 1 from each of the implants listed in Table 2. The average daily amount (ng/day) of Compound 1 released from each implant over time in vitro is listed in Table 2. As shown by FIGS. 2 and 9, Implants 1-4 and 9 released Compound 1 at a constant or near zero order rate continuously with little or no lag period for sustained periods. Implant 5 released little drug (Compound 1) in vitro during the first two months in release medium and then released a sharp burst of the drug equal to about 80% of the initial load (FIG. 5). Implant 6, similarly, failed to release any significant amount of drug even after two full months of incubation in the release medium (FIG. 3).

In addition, it was found surprisingly that when the amount of Compound 1 in the implant exceeded 8% by weight, implants produced a significant burst of drug release and/or provided very fast release rates that were generally considered to be unsuitable for the intended therapeutic uses. For example, implant 7 released about 55% of its drug load on day 1 with only a modest amount of drug release thereafter (FIG. 4). Implant 8 released over 70% of its drug load during the first two weeks in release medium (FIG. 4).

When tested in dogs, each of the four implants (Implants 1-4; see Table 2) reduced intraocular pressure in the eye on average between 20% and 30% from the baseline IOP, depending on the formulation (FIGS. 5-8). The duration of the IOP-lowering effect in the eye produced by each of the prostamide (Compound 1)-containing implants, lasted for at least 120 days after placement of the implant in the anterior chamber of the eye.

Figure 10:
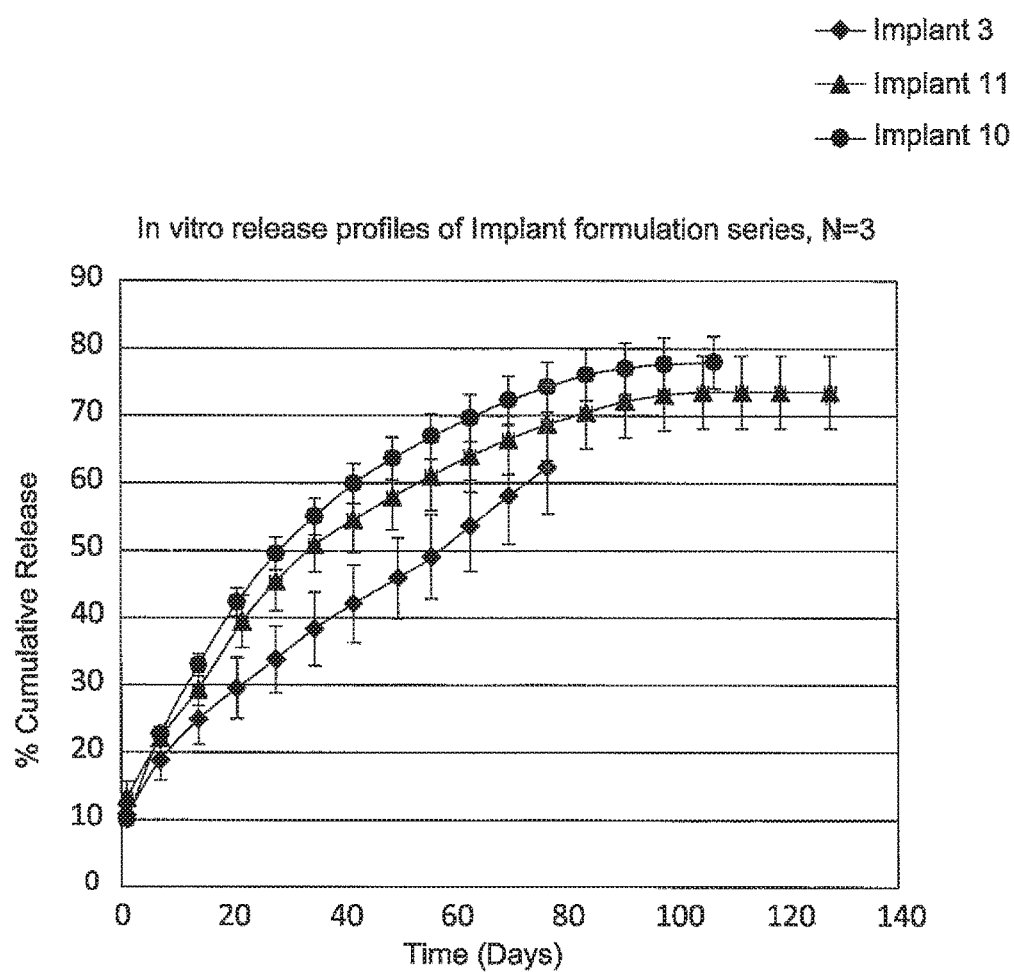
FIG. 10 shows the in vitro cumulative total percent release of Compound 1 into phosphate buffered saline (0.01 M; pH 7.4) at 37° C. over time from Implant Nos. 3, 10, and 11, prepared with a twin screw extruder. The compositions of Implants 3, 10, and 11 are set forth in Table 2.

The stability of Compound 1 in Implant No. 3 (as measured by the formation of impurity following storage at 25° C. or 30° C. for 1.5 months and 3 months) was improved by incorporating an antioxidant into the formulation of Implant No. 3 (Implants 10 and 11). For example, the inclusion of 2.0% ascorbic acid with a corresponding adjustment in the weight percentage of the three polymers (as in Implant No. 11) decreased the % total impurity formed in the implant after 1.5 and 3 months of storage at 25° C. or 30° C. as compared to the % total impurity formed during those periods in an implant having Formulation No. 3 (Table 3). Similarly, the inclusion of 2.0% butylated hydroxyanisole (BHA) and 0.5% EDTA with a corresponding adjustment in the weight percentage of the three polymers (as in Implant No. 10) decreased the % total impurity formed in the implant after 1.5 and 3 months of storage as compared to the % total impurity formed during those same periods in an Implant having Formulation No. 3 (Table 3). Thus, including an antioxidant enhances the stability of Compound 1, thereby extending the shelf life and preserving the potency of the manufactured implant. The inclusion of EDTA, a metal chelating agent, may add to the stability. The percent cumulative in vitro release of Compound from each of Implants 10 and 11 as compared to that of Implant 3 are shown in (FIG. 10).

TABLE 2

Extruded implants prepared and tested according to Example 2.

| Implant No. | Composition (Formulation) (% w/w) | Implant dimensions (diameter × length) | Implant weight (μg) | Release rate In vitro (ng/day) | Estimated release duration (months) |
| --- | --- | --- | --- | --- | --- |
| 1 | 8.0% Compound 1<br>92.0% R202H | 150 μm × 1.5 mm | 36 | 29 | 3 |
| 2 | 8.0% Compound 1<br>92.0% R203H | 200 μm × 1.5 mm | 64 | 26 | 6 |
| 3 | 8.0% Compound 1<br>51.7% R203S<br>23.0% RG752S<br>11.5% R202H<br>5.8% hexadecanol | 200 μm × 1.5 mm | 64 | 34 | 4-5 |
| 4 | 8.0% Compound 1<br>18.4% R203S<br>73.6% R203H | 200 μm × 1.5 mm | 64 | 28 | 6 |
| 5 | 8.1% Compound 1<br>91.9% RG755S | 200 μm × 1.5 mm | 64 | ~0 for first 50 days | |
| 6 | 8.1% Compound 1<br>91.9% R203S | 200 μm × 1.5 mm | 64 | ~0 | |
| 7 | 12% Compound 1<br>49.5% R203S<br>22.0% RG752S<br>11.0% R202H<br>5.5% PEG 3350 | 200 μm × 1.5 mm | 64 | Day 1 release: 4147 ng Next 3 months: 21 ng/day | |
| 8 | 10% Compound 1<br>90% R202H | 200 μm × 1.5 mm | 64 | 224 | 1 |
| 9 | 8.0% Compound 1<br>92.0% R202H | 250 μm × 1.5 mm | 100 | 80 | 3 |
| 10 | 8.0% Compound 1<br>50.3% R203S<br>22.4% RG752S<br>11.2% R202H<br>5.6% hexadecanol<br>2.0% BHA<br>0.5% EDTA | 200 μm × 1.5 mm | 64 | 35 | 3-5 |

TABLE 2-continued

Extruded implants prepared and tested according to Example 2.

| Implant No. | Composition (Formulation) (% w/w) | Implant dimensions (diameter × length) | Implant weight (μg) | Release rate In vitro (ng/day) | Estimated release duration (months) |
|---|---|---|---|---|---|
| 11 | 8.0% Compound 1<br>50.6% R203S<br>22.5% RG752S<br>11.3% R202H<br>5.6% hexadecanol<br>2.0% ascorbic acid | 200 μm × 1.5 mm | 64 | 31 | 3-5 |

RESOMER ® RG755S is a poly(D,L-lactide-co-glycolide) having an ester end group and an inherent viscosity of about 0.50-0.70 dl/g (as measured for a 0.1% solution in chloroform at 25° C.), and a D,L-lactide:glycolide molar ratio of about 75:25.

PEG 3350 = polyethylene glycol having an average molecular weight of 3,350.

Hexadecanol = hexadecan-1-ol (cetyl alcohol)

BHA = butylated hydroxyanisole

EDTA = ethylenediaminetetraacetic acid

Compound 1 is a prostamide having the following structure:

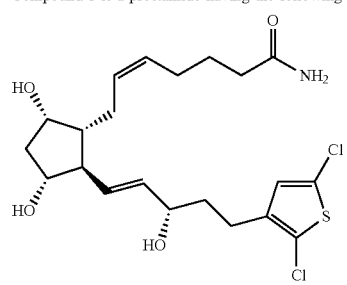

Compound 1

Compound 1

TABLE 3

Stability Study of Extruded Implants with and without antioxidants[1]

| Implant No. (Formulation) | % total impurity formed at 25° C./60% Relative humidity (Area %) | | | % total impurity formed at 30° C./65% Relative humidity (Area %) | | |
|---|---|---|---|---|---|---|
| | Time = 0 | 1.5 months | 3 months | Time = 0 | 1.5 months | 3 months |
| 3 | 4.34 | 7.57 | 9.10 | 4.34 | 7.61 | 8.54 |
| 10 | 3.82 | 4.85 | 4.97 | 3.82 | 4.80 | 5.05 |
| 11 | 3.83 | 5.03 | 5.30 | 3.82 | 4.94 | 5.66 |

[1]Following manufacture, implants were stored in a sealed aluminum pouch containing a desiccant and oxygen absorber pack after the pouch was purged with nitrogen.

What is claimed is:

1. A method for reducing intraocular pressure in a patient, comprising administering a biodegradable implant comprising a biodegradable polymer material, hexadecan-1-ol, and about 8% by weight of a compound having the formula

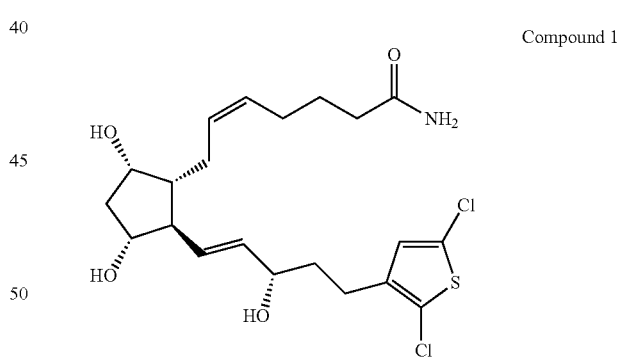

Compound 1 wherein the compound and the hexadecan-1-ol are associated with the biodegradable polymer material, and wherein the biodegradable polymer material comprises i) a poly(D,L-lactide) having an ester end group and an inherent viscosity of 0.25-0.35 dl/g, ii) a poly(D,L-lactide) having an acid end group and an inherent viscosity of 0.16-0.24 dl/g, and iii) a poly(D,L-lactide-co-glycolide) having an ester end group, an inherent viscosity of 0.16-0.24 dl/g, and a D,L-lactide:glycolide molar ratio of about 75:25, wherein the inherent viscosity of each poly(D,L-lactide) and poly(D,L-lactide-co-glycolide) polymer as given above is measured for a 0.1% solution of the polymer in chloroform at 25° C.

2. The method of claim 1, wherein the patient has elevated intraocular pressure, ocular hypertension, or glaucoma.

3. The method of claim 2, wherein the intraocular implant reduces the intraocular pressure in the eye by at least 30%, relative to the intraocular pressure in the eye before receiving the implant, for 3-5 months or more following placement in the eye.

\* \* \* \* \*

UNITED STATES PATENT AND TRADEMARK OFFICE
CERTIFICATE OF CORRECTION

PATENT NO. : 9,889,142 B2
APPLICATION NO. : 15/075922
DATED : February 13, 2018
INVENTOR(S) : Patrick M. Hughes et al.

It is certified that error appears in the above-identified patent and that said Letters Patent is hereby corrected as shown below:

On the Title Page

In item (56), in Column 2, under "Other Publications", Line 3, delete "Chemica" and insert -- Chimica --, therefor.

On the page 2, in Column 2, under "Other Publications", Line 8, delete "(prostamides prostaglandin-" and insert -- prostamides (prostaglandin- --, therefor.

In the Drawings

On sheet 2 of 10, in Figure 2, Line 5, delete "37°C" and insert -- 37° C. --, therefor.

On sheet 3 of 10, in Figure 3, Line 3, delete "37°C" and insert -- 37° C. --, therefor.

On sheet 4 of 10, in Figure 4, Line 3, delete "37°C" and insert -- 37° C. --, therefor.

On sheet 9 of 10, in Figure 9, Line 2, delete "37°C" and insert -- 37° C. --, therefor.

In the Specification

In Column 4, Lines 30-41, delete " 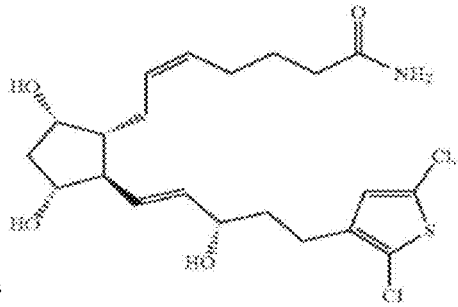 " and

Signed and Sealed this
Tenth Day of July, 2018

Andrei Iancu
*Director of the United States Patent and Trademark Office* insert -- 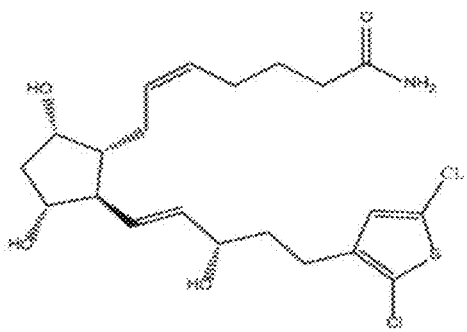 --, therefor.
In Column 4, Lines 51-64, delete " 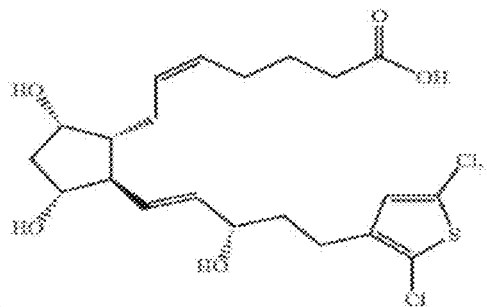 " and
insert -- 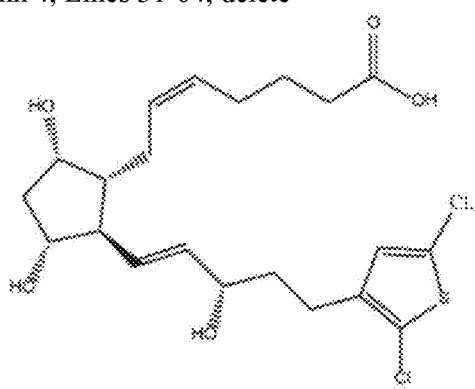 --, therefor.
In Column 15, Lines 46-55, delete " 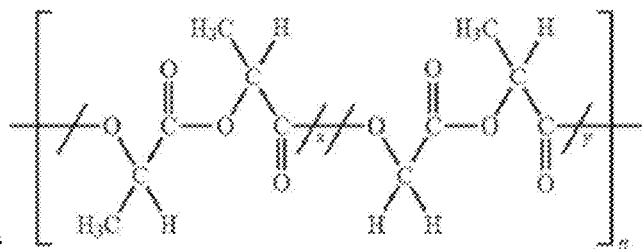 " and

CERTIFICATE OF CORRECTION (continued)
U.S. Pat. No. 9,889,142 B2

Page 3 of 3 insert -- 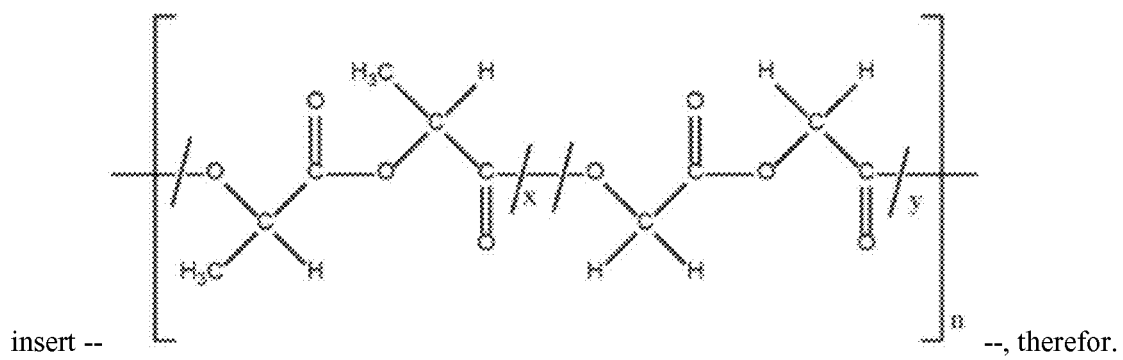 --, therefor.

In Column 26, Lines 1-14, delete " 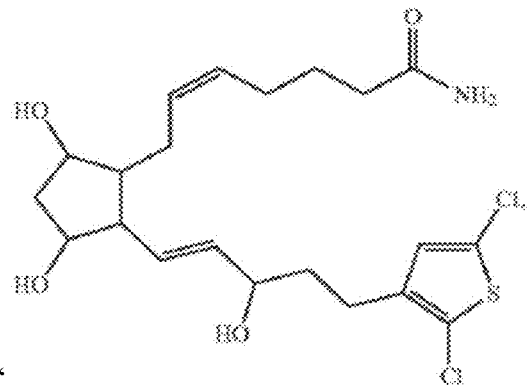 " and insert -- 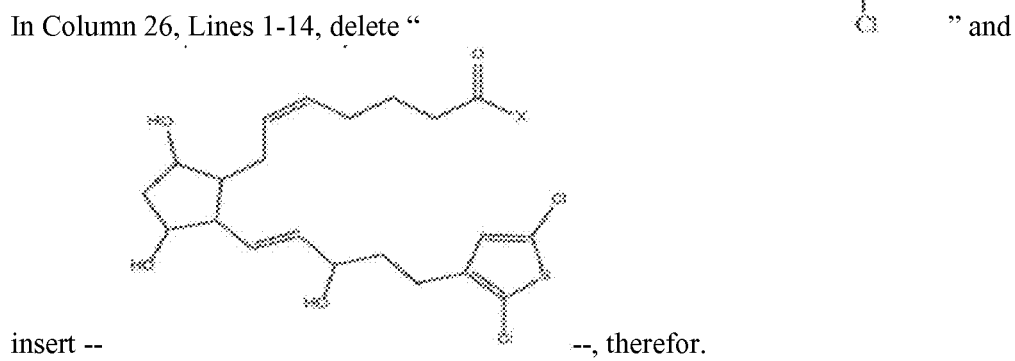 --, therefor.

In Column 35, Line 22 (in Table 2-continued), above "TABLE 3" delete "Compound 1".

In the Claims

In Column 36, Lines 40-52, in Claim 1, after " 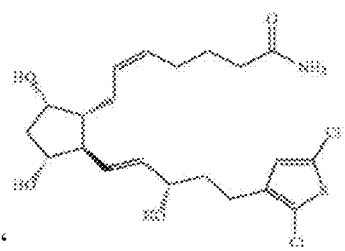 " insert -- , --.